(12) United States Patent
Penner

(10) Patent No.: US 9,581,605 B2
(45) Date of Patent: Feb. 28, 2017

(54) TRAPPING REAGENTS FOR REACTIVE METABOLITES SCREENING

(71) Applicant: Biogen MA Inc., Cambridge, MA (US)

(72) Inventor: Natalia Penner, Newton, MA (US)

(73) Assignee: Biogen MA Inc., Cambridge, MA (US)

( * ) Notice: Subject to any disclaimer, the term of this patent is extended or adjusted under 35 U.S.C. 154(b) by 136 days.

(21) Appl. No.: 14/402,818

(22) PCT Filed: May 22, 2013

(86) PCT No.: PCT/US2013/042246
§ 371 (c)(1),
(2) Date: Nov. 21, 2014

(87) PCT Pub. No.: WO2013/177293
PCT Pub. Date: Nov. 28, 2013

(65) Prior Publication Data
US 2015/0168430 A1 Jun. 18, 2015

Related U.S. Application Data

(60) Provisional application No. 61/650,448, filed on May 22, 2012.

(51) Int. Cl.
| | | |
|---|---|---|
| C12Q 1/32 | (2006.01) | |
| G01N 33/94 | (2006.01) | |
| C07K 5/02 | (2006.01) | |
| G01N 33/68 | (2006.01) | |
| C07K 5/062 | (2006.01) | |

(52) U.S. Cl.
CPC .............. *G01N 33/94* (2013.01); *C07K 5/0215* (2013.01); *C07K 5/0606* (2013.01); *G01N 33/6848* (2013.01); *Y02P 20/55* (2015.11)

(58) Field of Classification Search
CPC ... C07K 5/0215; C07K 5/0606; G01N 33/684; G01N 33/94; Y02P 20/55
See application file for complete search history.

(56) References Cited

U.S. PATENT DOCUMENTS

| 7,169,576 B2 | 1/2007 | Gan et al. |
| 2004/0248234 A1 | 12/2004 | Cole et al. |

FOREIGN PATENT DOCUMENTS

| WO | WO 2008/141012 A2 | 11/2008 |
| WO | WO 2009/071601 A1 | 6/2009 |
| WO | WO 2011/025366 A1 | 3/2011 |
| WO | WO 2011/159685 A2 | 12/2011 |

OTHER PUBLICATIONS

Soglia et al. J. Pharmaceutical Biomed. Anal. (2004) 36: 105-116.*
Moss et al .J. Am. Chem. Soc. (1978) 100(18): 5920-5927.*
Johnston et al. Analytical Chem. (1968) 40(12): 1837-1840.*
International Search Report and Written Opinion mailed Aug. 14, 2013 for International Application No. PCT/US2013/042246.
International Preliminary Report on Patentability mailed Dec. 4, 2014 for International Application No. PCT/US2013/042246.
Baillie et al., The use of mass spectrometry in the study of chemically-reactive drug metabolites. Application of MS/MS and LC/MS to the analysis of glutathione- and related S-linked conjugates of N-methylformamide. J Pharm Biomed Anal. 1989;7(12):1351-60.
Barry et al., Derivatisation for liquid chromatography/electrospray mass spectrometry: synthesis of pyridinium compounds and their amine and carboxylic acid derivatives. Rapid Commun Mass Spectrom. 2003;17(6):603-20.
Gan et al., Dansyl glutathione as a trapping agent for the quantitative estimation and identification of reactive metabolites. Chem Res Toxicol. May 2005;18(5):896-903.
Guengerich, Principles of covalent binding of reactive metabolites and examples of activation of bis-electrophiles by conjugation. Arch Biochem Biophys. Jan. 15, 2005;433(2):369-78.
Johnson, Alkyldimethylaminoethyl ester iodides for improved analysis of fatty acids by electrospray ionization tandem mass spectrometry. Rapid Commun Mass Spectrom. 2000;14(21):2019-24.
Kalgutkar et al., A comprehensive listing of bioactivation pathways of organic functional groups. Curr Drug Metab. Jun. 2005;6(3):161-225.
Lamos et al., Relative quantification of carboxylic acid metabolites by liquid chromatography-mass spectrometry using isotopic variants of cholamine. Anal Chem. Jul. 15, 2007;79(14):5143-9. Epub Jun. 12, 2007.
Ma et al., Detecting and characterizing reactive metabolites by liquid chromatography/tandem mass spectrometry. J Mass Spectrom. Sep. 2006;41(9):1121-39.
Mirzaei et al., Enhancing electrospray ionization efficiency of peptides by derivatization. Anal Chem. Jun. 15, 2006;78(12):4175-83.
Mitamura et al., Identification of bile acid S-acyl glutathione conjugates in rat bile by liquid chromatography/electrospray ionization-linear ion trap mass spectrometry. Steroids. Jan. 2011;76(1-2):68-77. doi: 10.1016/j.steroids.2010.09.002. Epub Sep. 15, 2010.
Moss et al., Micellar diastereoselectivity—tripeptide substrates. Tetrahedron Letters. 1981;22(4):283-6.

(Continued)

*Primary Examiner* — Susan Hanley
(74) *Attorney, Agent, or Firm* — Wolf, Greenfield & Sacks, P.C.

(57) ABSTRACT

The present invention provides compounds of Formula (I) and (II): (I) (II) wherein $R^1$, $R^2$, $R^4$, $R^5$, $R^6$, X and n are as defined herein, and wherein $R^3$ is hydrogen or a sulfur protecting group. Compounds of Formula (I) and (II), wherein R is hydrogen, may be useful in methods for detecting a reactive metabolite in a sample, e.g., wherein the metabolite is generated from the metabolism of a test compound, and wherein the metabolite and the compound of Formula (I) or (II) react to form a detectable adduct, e.g., detectable by mass spectrometry.

20 Claims, 16 Drawing Sheets

(56) References Cited

OTHER PUBLICATIONS

Olson et al., Concordance of the toxicity of pharmaceuticals in humans and in animals. Regul Toxicol Pharmacol. Aug. 2000;32(1):56-67.

Soglia et al., A semiquantitative method for the determination of reactive metabolite conjugate levels in vitro utilizing liquid chromatography-tandem mass spectrometry and novel quaternary ammonium glutathione analogues. Chem Res Toxicol. Mar. 2006;19(3):480-90.

Srivastava et al., Role of reactive metabolites in drug-induced hepatotoxicity. Handb Exp Pharmacol. 2010;(196):165-94. doi: 10.1007/978-3-642-00663-0_7.

Yang et al., Enhancement of amino acid detection and quantification by electrospray ionization mass spectrometry. Anal Chem. Jul. 1, 2006;78(13):4702-8.

Zheng et al., Screening and identification of GSH-trapped reactive metabolites using hybrid triple quadruple linear ion trap mass spectrometry. Chem Res Toxicol. May 2007;20(5):757-66. Epub Apr. 3, 2007.

\* cited by examiner

| Index | RT | m/z | Mass Defect | TIC | Num Merged | Quality |
|---|---|---|---|---|---|---|
| 1848 | 6.66 | 768.5541 | 0.5541 | 5.0e4 | 1 | 75 |
| 1829 | 6.62 | 768.5797 | 0.5797 | 5.8e4 | 1 | 77 |
| 1901 | 6.78 | 768.5854 | 0.5854 | 6.3e4 | 1 | 75 |
| 1928 | 6.84 | 768.5903 | 0.5903 | 5.6e4 | 1 | 75 |
| 1908 | 6.80 | 768.5906 | 0.5906 | 5.8e4 | 1 | 76 |
| 1778 | 6.51 | 769.5546 | 0.5546 | 2.2e4 | 1 | 67 |
| 1920 | 6.82 | 769.5941 | 0.5941 | 3.0e4 | 1 | 64 |
| 2002 | 7.00 | 770.5571 | 0.5571 | 6.9e4 | 1 | 75 |
| 1964 | 6.92 | 771.5731 | 0.5731 | 3.1e4 | 1 | 75 |
| 1951 | 6.89 | 771.6358 | 0.6358 | 2.5e4 | 1 | 68 |
| 1988 | 6.97 | 772.0756 | 0.0756 | 4.1e4 | 1 | 74 |
| 1898 | 6.77 | 772.5258 | 0.5258 | 6.8e4 | 1 | 83 |
| 1885 | 6.75 | 772.5275 | 0.5275 | 6.9e4 | 1 | 84 |
| 1465 | 5.67 | 772.5834 | 0.5834 | 3.0e3 | 1 | 77 |
| 1571 | 5.94 | 773.5871 | 0.5871 | 5.0e3 | 1 | 73 |
| 1622 | 6.09 | 774.5904 | 0.5904 | 4.8e3 | 1 | 64 |
| 1326 | 5.18 | 776.0471 | 0.0471 | 2.1e3 | 1 | 46 |
| 1316 | 5.12 | 776.0499 | 0.0499 | 2.2e3 | 1 | 38 |
| 848 | 3.68 | 776.3999 | 0.3999 | 8.3e3 | 1 | 51 |
| 601 | 2.80 | 778.3625 | 0.3625 | 1.1e4 | 1 | 76 |
| 604 | 2.81 | 778.3630 | 0.3630 | 8.7e3 | 1 | 75 |
| 597 | 2.78 | 778.3631 | 0.3631 | 1.8e4 | 1 | 85 |
| 608 | 2.82 | 778.3640 | 0.3640 | 6.1e3 | 1 | 61 |
| 596 | 2.77 | 778.3647 | 0.3647 | 1.8e4 | 1 | 80 |
| 594 | 2.77 | 778.3655 | 0.3655 | 1.6e4 | 1 | 76 |
| 1792 | 6.54 | 778.5361 | 0.5361 | 9.6e3 | 1 | 69 |
| 1887 | 6.75 | 778.5368 | 0.5368 | 1.6e4 | 1 | 69 |
| 1695 | 6.31 | 778.5618 | 0.5618 | 3.2e3 | 1 | 14 |
| 599 | 2.79 | 779.3659 | 0.3659 | 6.7e3 | 1 | 70 |
| 1691 | 6.29 | 779.5500 | 0.5500 | 5.2e3 | 1 | 53 |
| 1881 | 6.74 | 780.4859 | 0.4859 | 1.4e5 | 1 | 84 |
| 1840 | 6.64 | 780.5453 | 0.5453 | 9.8e4 | 1 | 76 |
| 1671 | 6.23 | 780.5509 | 0.5509 | 3.6e4 | 1 | 78 |
| 1660 | 6.20 | 780.5516 | 0.5516 | 3.3e4 | 1 | 78 |
| 1667 | 6.22 | 780.5774 | 0.5774 | 3.1e4 | 1 | 79 |
| 1844 | 6.65 | 781.5477 | 0.5477 | 4.5e4 | 1 | 66 |
| 1678 | 6.25 | 781.5545 | 0.5545 | 2.6e4 | 1 | 73 |
| 1992 | 6.98 | 781.5572 | 0.5572 | 3.6e4 | 1 | 81 |
| 1972 | 6.93 | 782.5135 | 0.5135 | 7.3e5 | 1 | 92 |
| 1935 | 6.86 | 782.5656 | 0.5656 | 3.3e5 | 1 | 90 |
| 2000 | 6.99 | 782.5657 | 0.5657 | 8.0e5 | 1 | 93 |
| 1947 | 6.88 | 782.5661 | 0.5661 | 4.7e5 | 1 | 90 |
| 1289 | 5.02 | 782.5663 | 0.5663 | 3.7e3 | 1 | 72 |

Fig. 4

| Index | RT | m/z | Mass Defect | TIC | Num Merged | Quality |
|---|---|---|---|---|---|---|
| 644 | 2.94 | 431.2540 | 0.2540 | 4.7e2 | 1 | 18 |
| 815 | 4.12 | 432.2355 | 0.2355 | 1.2e3 | 1 | 47 |
| 819 | 4.13 | 432.2378 | 0.2378 | 1.1e3 | 1 | 39 |
| 813 | 4.10 | 432.2378 | 0.2378 | 1.6e3 | 1 | 58 |
| 877 | 4.33 | 432.2384 | 0.2384 | 1.0e4 | 1 | 76 |
| 874 | 4.32 | 432.2385 | 0.2385 | 5.7e3 | 1 | 69 |
| 418 | 1.56 | 432.2796 | 0.2796 | 2.3e2 | 1 | 16 |
| 421 | 1.59 | 432.2802 | 0.2802 | 2.5e2 | 1 | 12 |
| 581 | 2.73 | 433.2709 | 0.2709 | 1.7e2 | 1 | 0 |
| 577 | 2.71 | 433.2716 | 0.2716 | 1.1e2 | 1 | 0 |
| 1230 | 5.93 | 433.2925 | 0.2925 | 5.3e3 | 1 | 12 |
| 1226 | 5.92 | 433.2937 | 0.2937 | 6.9e3 | 1 | 17 |
| 887 | 4.38 | 434.2398 | 0.2398 | 4.9e2 | 1 | 34 |
| 1235 | 5.94 | 434.2923 | 0.2923 | 1.7e3 | 1 | 0 |
| 1137 | 5.65 | 435.2514 | 0.2514 | 2.1e2 | 1 | 0 |
| 1170 | 5.79 | 436.2553 | 0.2553 | 1.6e2 | 1 | 0 |
| 820 | 4.13 | 437.1944 | 0.1944 | 4.9e2 | 1 | 0 |
| 816 | 4.12 | 438.1934 | 0.1934 | 3.0e2 | 1 | 0 |
| 545 | 2.42 | 438.1959 | 0.1959 | 1.1e4 | 1 | 71 |
| 883 | 4.36 | 439.1995 | 0.1995 | 1.5e2 | 1 | 0 |
| 550 | 2.44 | 439.1997 | 0.1997 | 2.9e3 | 1 | 34 |
| 508 | 2.29 | 440.2121 | 0.2121 | 2.0e4 | 1 | 72 |
| 516 | 2.31 | 440.2123 | 0.2123 | 2.3e4 | 1 | 64 |
| 534 | 2.36 | 440.2125 | 0.2125 | 2.6e4 | 1 | 66 |
| 512 | 2.30 | 440.2125 | 0.2125 | 2.6e4 | 1 | 65 |
| 536 | 2.37 | 440.2126 | 0.2126 | 2.4e4 | 1 | 82 |
| 520 | 2.31 | 440.2128 | 0.2128 | 1.8e4 | 1 | 59 |
| 540 | 2.38 | 440.2128 | 0.2128 | 1.4e4 | 1 | 66 |
| 537 | 2.37 | 440.2129 | 0.2129 | 2.0e4 | 1 | 70 |
| 524 | 2.32 | 440.2129 | 0.2129 | 2.4e4 | 1 | 64 |
| 530 | 2.34 | 440.2132 | 0.2132 | 4.0e4 | 1 | 78 |
| 527 | 2.33 | 440.2134 | 0.2134 | 3.3e4 | 1 | 76 |
| 532 | 2.35 | 440.2137 | 0.2137 | 3.6e4 | 1 | 77 |
| 1072 | 5.37 | 441.3325 | 0.3325 | 1.7e2 | 1 | 0 |
| 713 | 3.29 | 442.3379 | 0.3379 | 1.6e2 | 1 | 4 |
| 717 | 3.31 | 442.3390 | 0.3390 | 1.9e2 | 1 | 0 |
| 1314 | 6.17 | 442.3540 | 0.3540 | 6.6e2 | 1 | 9 |
| 1081 | 5.40 | 444.3328 | 0.3328 | 3.7e3 | 1 | 52 |
| 241 | 0.81 | 445.2169 | 0.2169 | 2.4e4 | 1 | 79 |
| 229 | 0.78 | 445.2171 | 0.2171 | 2.4e4 | 1 | 78 |
| 201 | 0.72 | 445.2173 | 0.2173 | 2.2e4 | 1 | 76 |
| 268 | 0.87 | 445.2178 | 0.2178 | 1.3e4 | 1 | 72 |
| 908 | 4.45 | 445.2178 | 0.2178 | 9.6e2 | 1 | 26 |

Fig. 5

TRAPPING REAGENTS FOR REACTIVE METABOLITES SCREENING

RELATED APPLICATIONS

The present application is a national stage filing under 35 U.S.C. §371 of international PCT application, PCT/US2013/042246, filed May 22, 2013, which claims priority under 35 U.S.C. §119(e) to U.S. provisional patent application, U.S. Ser. No. 61/650,448, filed May 22, 2012, each of which is incorporated herein by reference.

BACKGROUND

Drug induced toxicity remains one of the major reasons for the failure of drug candidates to be approved and the withdrawal of approved drugs from the market. See, e.g., Olson et al., *Regul. Toxicol. Pharmacol.* (2000) 32:56-67. Chemically reactive electrophilic metabolites of the drug are likely mediators of the toxicity, possibly by acting as covalent modifiers of essential cellular machinery. See, e.g., Guengerich et al., *Arch. Biochem. Biophys.* (2005) 433:369-378; Kalgutkar et al., *Curr. Drug. Metab.* (2005) 6:161-225. Often drugs undergo biotransformation to metabolites that can interfere with cellular functions through their intrinsic chemical reactivity towards glutathione (GSH), leading to GSH depletion, and towards other functionally critical macromolecules, resulting in reversible modification, irreversible adduct formation, or irreversible loss of activity. See, e.g., Srivastava et al., *Handb. Exp. Pharmacol.* (2010) 196:165-194. There is now a great deal of evidence which shows that reactive metabolites are formed from drugs known to cause hepatotoxicity, such as acetaminophen, tamoxifen, isoniazid, and amodiaquine.

Preclinical screens have been developed in an effort to minimize bioactivation liabilities in the early stages of drug discovery. See, e.g., Ma and Subramanian, *J. Mass. Spectrom.* (2006) 41:1121-1139. The most common analytical techniques used in preclinical screens are gas chromatography (GC) or liquid chromatography (LC) coupled to mass spectrometry (MS), e.g., such as GC or LC coupled to tandem mass spectrometry (MS/MS) scanning. Mass spectrometry offers a much greater sensitivity than alternative methods, such as nuclear magnetic resonance (NMR) spectroscopy, and thus affords the analysis of numerous low abundance metabolites, but its quantitative precision is inherently poorer. One strategy for improving the detection of metabolites by mass spectrometry involves treating the sample with a "heavy" and "light" version of an isotopic labeling reagent, thereby creating a "heavy" and "light" version of the labeled metabolite. See, e.g., Lamos et al., *Anal. Chem.* (2007) 79:5143-5149. Installing a positively-charged functional group has also been found to enhance the ion efficiency and corresponding high detection sensitivity in positive ion mode electrospray ionization-mass spectrometry (ESI-MS). See, e.g., Lamos in supra, Yang et al., *Anal. Chem.* (2006) 78:4702-4708; Johnson, *Rapid Commun. Mass. Spectrom.* (2000) 14:2019-2024; Barry et al., *Rapid Commun. Mass. Spectrom.* (2003) 17:603-620; Mirzaei et al., *Anal. Chem.* (2006) 78:4175-4183; Soglia et al., *Chem. Res. Toxicol.* (2006) 19:480-490; and U.S. Patent Application No. 2004/0248234.

However, despite these efforts, there continues to remain a need for additional improvement and development of early screening assays to identify and/or quantify potential chemically reactive electrophilic metabolites which may be responsible for drug-induced toxicity.

SUMMARY OF THE INVENTION

Investigators have looked to glutathione (GSH) as a promising trapping reagent since most compounds undergoing bioactivation have been known to generate soft electrophiles that may be trapped with a free thiol. See, e.g., Baille et al., *J. Pharm. Biomed. Anal.* (1989) 7:1351-1360. While tritiated GSH trapping allows direct quantification of conjugates, adequate separation of the [$^3$H]GSH adducts from unreacted material has proven challenging and often results in insufficient sensitivity. See, e.g., Soglia et al., *Chem. Res. Toxicol.* (2006) 19:480-490 and U.S. Patent Application No. 2004/0248234. Use of a GSH analogue tethered to a fluorescent dansyl tag has been used to circumvent the use of a radiolabel, but the method still requires HPLC separation of fluorescently labeled conjugate from unreacted starting material. See, e.g., Gan et al., *Chem. Res. Toxicol.* (2005) 18:896-903 and U.S. Pat. No. 7,169,576. Soglia and co-workers have since developed a quaternary ammonium GSH analogue (QA-GSH) containing a fixed positive charge which appears amenable to high throughput screening and does not require HPLC separation. See, e.g., Soglia in supra. Others have used multiple reaction monitoring (MRM) as the survey scan to trigger the acquisition of enhanced product ion (EPI) spectra on a triple quadrupole linear ion mass spectrometer using protonated GSH adducts. See, e.g., Zheng et al., *Chem. Res. Toxicol.* (2007) 20:757-766. At present, however, the sensitivity of GSH screening assays are not always satisfactory. Additionally, the current approach is not good for quantitation due to the variation of chromatography and ion suppression from run to run and from sample to sample.

Aspects of the present invention are based, at least in part, on the observation that cysteine modified with the quaternary amine cholamine ("cys-chol"), as a labeling reagent, engenders a higher ionization efficiency and corresponding detection sensitivity compared to either unmodified cysteine or GSH, thus allowing for the improved identification of additional, heretofore unknown, reactive electrophilic metabolites in drug samples.

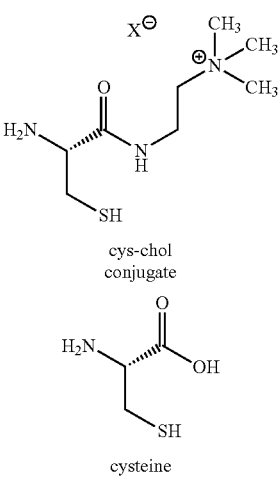

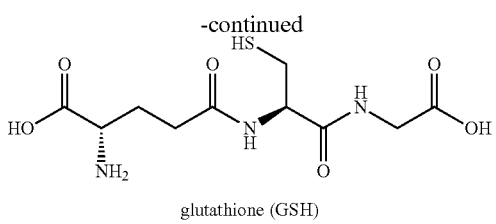

glutathione (GSH)

It is envisioned other thiol containing compounds conjugated to cholamine may have similar improved detection sensitivity. By way of example, it is envisioned glutathione modified with cholamine will have a similar improved detection sensitivity.

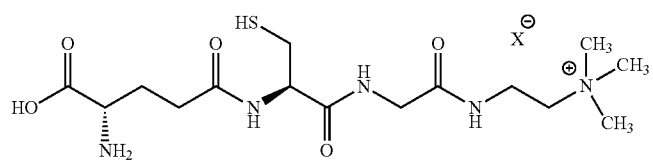

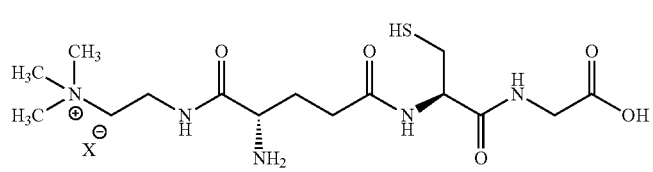

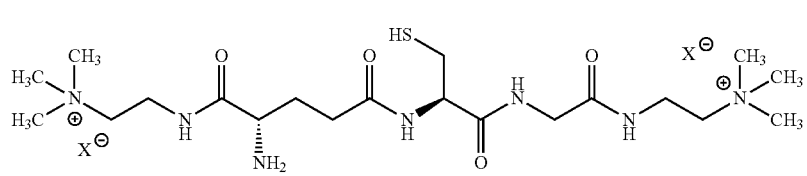

GSH-chol conjugates

A broad application of this discovery is further envisioned, extending the applicability to other quaternary amines other than cholamine, conjugated to thiols other than cysteine or GSH, for use as labeling reagents for the detection of reactive electrophilic metabolites in drug samples.

Thus, in certain aspects, the present invention provides new labeling reagents, encompassing cys-chol conjugates, of Formula (I) for the trapping of metabolites:

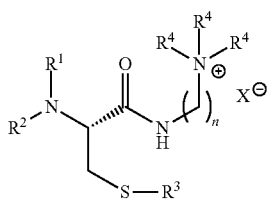

(I)

wherein $R^1$, $R^2$, $R^4$, X, and n are as defined herein, and $R^3$ is hydrogen when used as a labeling reagent, or $R^3$ is a sulfur protecting group.

In other aspects, the present invention provides new labeling reagents of Formula (II), encompassing GSH-chol conjugates, for the trapping of metabolites:

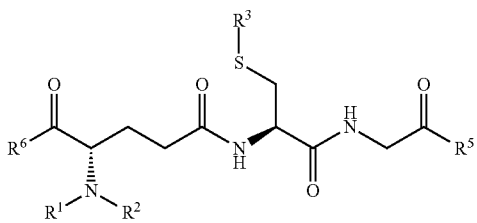

(II)

wherein $R^1$, $R^2$, $R^4$, X and n are as defined herein, $R^3$ is hydrogen when used as a labeling reagent, or $R^3$ is a sulfur protecting group, and at least one of $R^5$ and $R^6$ is a group of Formula (i):

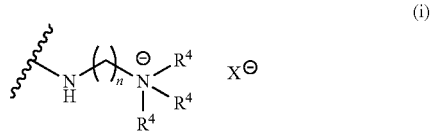

(i)

wherein $R^4$, X, and n are as defined herein.

In other aspects, the present invention provides methods for detecting a metabolite in a sample, the method comprising:

contacting a sample comprising a metabolite with a compound of Formula (I) or (II):

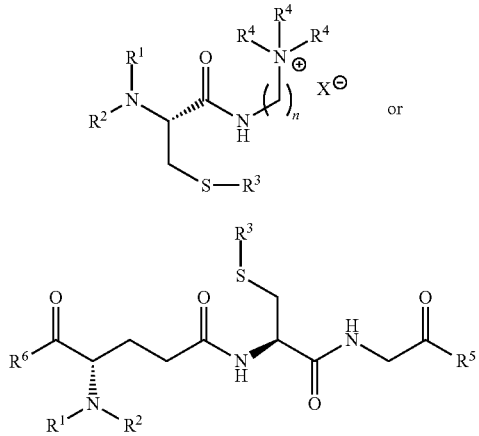

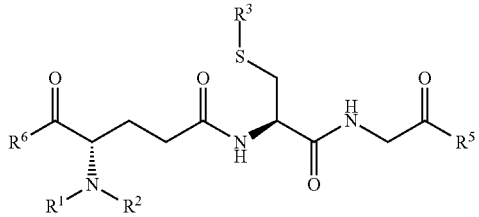

wherein $R^1$, $R^2$, $R^4$, $R^5$, $R^6$, X and n are as defined herein, and $R^3$ is hydrogen, wherein the metabolite and the compound of Formula (I) or (II) react to form an adduct; and detecting the adduct, e.g., by mass spectrometry.

In certain embodiments, the sample comprises an enzyme system. In certain embodiments, the sample comprises a test compound. In certain embodiments, the step of contacting further comprises contacting the sample comprising a test compound and the enzyme system, wherein the metabolite of the test compound is generated from metabolism by the enzyme system. In certain embodiments, the enzyme system is a P450 microsomal enzyme system. In certain embodiments, the P450 microsomal enzyme system is selected the group consisting of microsomes, S9 fractions, and P450 enzymes. In certain embodiments, the microsomes are mammalian liver microsomes, e.g., human liver microsomes. In certain embodiments, the S9 fraction is mammalian S9 fraction, e.g., human liver S9 fraction.

In certain embodiments, the adduct formed from the reaction of a compound of Formula (I) or (II) with the metabolite is initiated by addition of a NADPH-generating system or NADPH. In certain embodiments, the adduct formation is initiated by addition of NADPH.

In certain embodiments, the adduct is detected using mass spectrometry. In certain embodiments, the adduct is detected using liquid chromatography coupled to mass spectrometry. In certain embodiments, the mass spectrometry is electrospray ionization (ESI) coupled with tandem mass spectrometry (ESI-MS/MS). In certain embodiments, the liquid chromatography is high pressure liquid chromatography (HPLC). In certain embodiments, the liquid chromatography is ultra high pressure liquid chromatography (UPLC or UHPLC).

In another aspect, provided is a method for detecting a metabolite in a sample, the method comprising:

contacting a test compound, an enzyme system, and a compound of Formula (I) or (II):

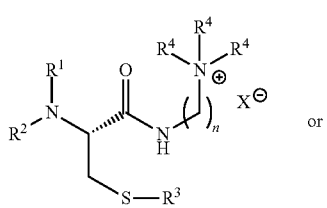

wherein $R^1$, $R^2$, $R^4$, $R^5$, $R^6$, X and n are as defined herein, and $R^3$ is hydrogen;

wherein the test compound is metabolized by the enzyme system to provide a metabolite; and wherein the metabolite reacts with a compound of Formula (I) or (II) to form an adduct; and detecting the adduct, e.g., by mass spectrometry.

In certain embodiments, the methods as described herein are methods for detecting low levels of already known metabolites. In certain embodiments, the methods as described herein are methods of identifying new metabolites. In certain embodiments, the methods as described herein are methods of improving the resolution or confidence of metabolite detection.

The details of one or more embodiments of the invention are set forth in the Detailed Description of Certain Embodiments, as described below. Other features, objects, and advantages of the invention will be apparent from the Definitions, Examples, Figures, and Claims.

DEFINITIONS

Figure 1A:
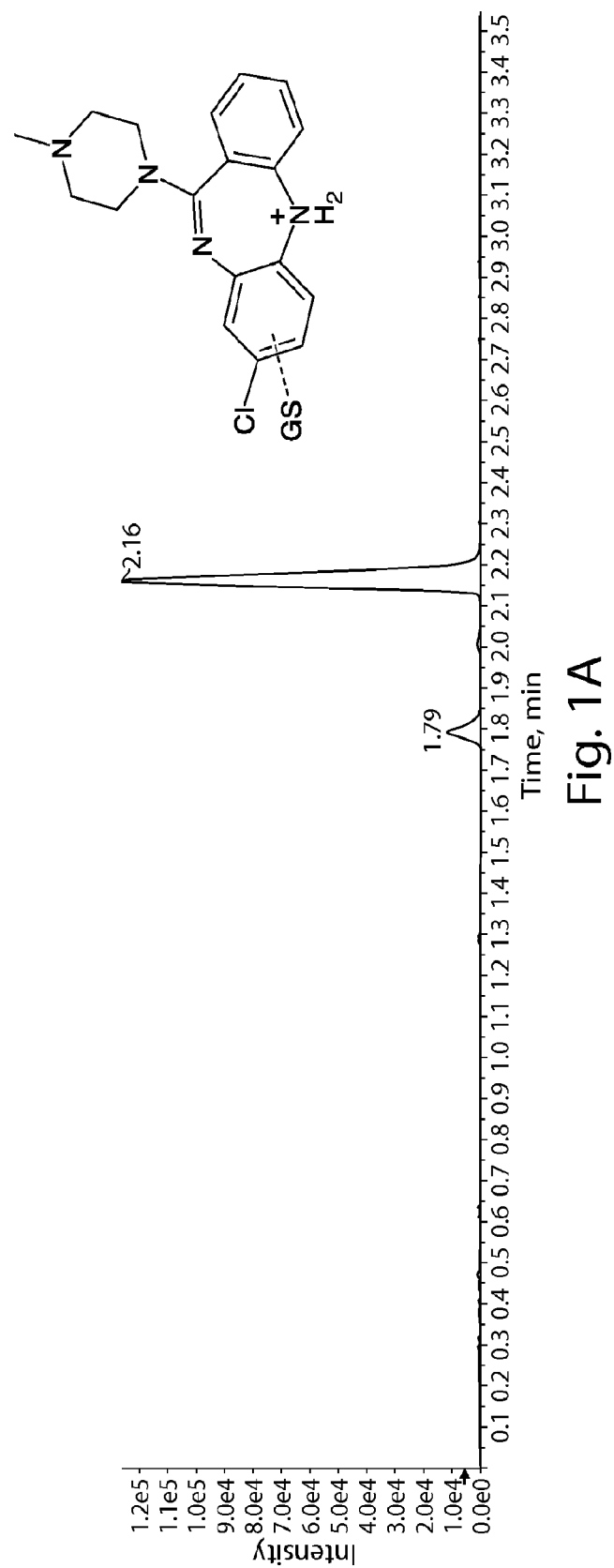
FIGS. 1A and 1B depict the LC-MS/MS analysis of GSH adduct formation with clozapine (+TOF MS-MS (100-1000): 632.21+/−0.05 Da) plus two reactive clozapine metabolites.

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or isomers can be prepared by asymmetric syntheses. See, for example, Jacques et al., Enantiomers, Racemates and Resolutions (Wiley Interscience, New York, 1981); Wilen et al., *Tetrahedron* 33:2725 (1977); Eliel, E. L. *Stereochemistry of Carbon Compounds* (McGraw-Hill, N.Y., 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-4}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_1$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl. In certain embodiments, the alkyl group is a substituted $C_{1-10}$ alkyl.

As used herein, "alkenyl" refers to a radical of a straight-chain or branched hydrocarbon group having from 2 to 10 carbon atoms and one or more carbon-carbon double bonds ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

As used herein, "alkynyl" refers to a radical of a straight-chain or branched hydrocarbon group having from 2 to 10 carbon atoms and one or more carbon-carbon triple bonds ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-7}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

As used herein, "carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_3$ 8 carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_3$ 8 carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-10}$ carbocyclyl. In certain embodiments, the carbocyclyl group is a substituted $C_{3-10}$ carbocyclyl.

In some embodiments, "carbocyclyl" is a monocyclic or bicyclic saturated carbocyclyl group having from 3 to 10 ring carbon atoms ("$C_{3-10}$ cycloalkyl"). In some embodiments, a cycloalkyl group has 3 to 8 ring carbon atoms ("$C_3$ 8 cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ unsaturated cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_3$ 8 cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-10}$ cycloalkyl. In certain embodiments, the cycloalkyl group is a substituted $C_{3-10}$ cycloalkyl.

As used herein, "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, thiorenyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo-[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14 it electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

As used herein, "heteroaryl" refers to a radical of a 5-14 membered monocyclic or polycyclic (e.g., bicyclic or tricyclic) 4n+2 aromatic ring system (e.g., having 6, 10, or 14 it electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

Alkyl, alkenyl, alkynyl, carbocyclyl, heterocyclyl, aryl, and heteroaryl groups, as defined herein, are substituted or unsubstituted, also referred to herein as "optionally substituted". In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SeH, —SeR$^{aa}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-50}$ alkyl, C$_{2-50}$ alkenyl, C$_{2-50}$ alkynyl, C$_3$-10 carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-50}$ alkyl, C$_{2-50}$ alkenyl, C$_{2-50}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-50}$ alkyl, C$_{2-50}$ alkenyl, C$_{2-50}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-50}$ alkyl, C$_{2-50}$ alkenyl, C$_{2-50}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-50}$ alkyl, C$_{2-50}$ alkenyl, C$_{2-50}$ alkynyl, C$_3$-10 carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-50}$ alkyl, C$_{2-50}$ alkenyl, C$_{2-50}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-50}$ alkyl, C$_{2-50}$ alkenyl, C$_{2-50}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-50}$ alkyl, —ON(C$_{1-50}$ alkyl)$_2$, —N(C$_{1-50}$ alkyl)$_2$, —N(C$_{1-50}$ alkyl)$_3$$^+$X$^-$, —NH(C$_{1-50}$ alkyl)$_2$$^+$X$^-$, —NH$_2$(C$_{1-50}$ alkyl)$^+$X$^-$, —NH$_3$$^+$X$^-$, —N(OC$_{1-50}$ alkyl)(C$_{1-50}$ alkyl), —N(OH)(C$_{1-50}$ alkyl), —NH(OH), —SH, —SC$_{1-50}$ alkyl, —SS(C$_{1-50}$ alkyl), —C(=O)(C$_{1-50}$ alkyl), —CO$_2$H, —CO$_2$(C$_{1-50}$ alkyl), —OC(=O)(C$_{1-50}$ alkyl), —OCO$_2$(C$_{1-50}$ alkyl), —C(=O)NH$_2$, —C(=O)N(C$_{1-50}$ alkyl)$_2$, —OC(=O)NH(C$_{1-50}$ alkyl), —NHC(=O)(C$_{1-50}$ alkyl), —N(C$_{1-50}$ alkyl)C(=O)(C$_{1-50}$ alkyl), —NHCO$_2$(C$_{1-50}$ alkyl), —NHC(=O)N(C$_{1-50}$ alkyl)$_2$, —NHC(=O)NH(C$_{1-50}$ alkyl), —NHC(=O)NH$_2$, —C(=NH)O(C$_{1-50}$ alkyl), —OC(=NH)(C$_{1-50}$ alkyl), —OC(=NH)OC$_{1-50}$ alkyl, —C(=NH)N(C$_{1-50}$ alkyl)$_2$, —C(=NH)NH(C$_{1-50}$ alkyl), —C(=NH)NH$_2$, —OC(=NH)N(C$_{1-50}$ alkyl)$_2$, —OC(NH)NH(C$_{1-50}$ alkyl), —OC(NH)NH$_2$, —NHC(NH)N(C$_{1-50}$ alkyl)$_2$, —NHC(=NH)

$-NH_2$, $-NHSO_2(C_{1-50}$ alkyl), $-SO_2N(C_{1-50}$ alkyl)$_2$, $-SO_2NH(C_{1-50}$ alkyl), $-SO_2NH_2$, $-SO_2C_{1-50}$ alkyl, $-SO_2OC_{50}$ alkyl, $-OSO_2C_{1-6}$ alkyl, $-SOC_{1-6}$ alkyl, $-Si(C_{1-50}$ alkyl)$_3$, $-OSi(C_{1-6}$ alkyl)$_3$-$C(=S)N(C_{1-50}$ alkyl)$_2$, $C(=S)NH(C_{1-50}$ alkyl), $C(=S)NH_2$, $-C(=O)S(C_{1-6}$ alkyl), $-C(=S)SC_{1-6}$ alkyl, $-SC(=S)SC_{1-6}$ alkyl, $-P(=O)_2(C_{1-50}$ alkyl), $-P(=O)(C_{1-50}$ alkyl)$_2$, $-OP(=O)(C_{1-50}$ alkyl)$_2$, $-OP(=O)(OC_{1-50}$ alkyl)$_2$, $C_{1-50}$ alkyl, $C_{2-50}$ alkenyl, $C_{2-50}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form $=O$ or $=S$;

wherein $X^-$ is a counteranion.

As used herein, the term "halo" or "halogen" refers to fluorine (fluoro, $-F$), chlorine (chloro, $-Cl$), bromine (bromo, $-Br$), or iodine (iodo, $-I$).

As used herein, a "counteranion" or "counter anion" is a negatively charged group associated with a positively charged quarternary amine. Exemplary counteranions include halide ions (e.g., $F^-$, $Cl^-$, $Br^-$, $I^-$), $NO_3^-$, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate), and carboxylate ions (e.g., acetate, ethanoate, propanoate, benzoate, glycerate, lactate, tartrate, glycolate).

Nitrogen atoms can be substituted or unsubstituted as valency permits, and include primary, secondary, tertiary, and quarternary nitrogen atoms. Exemplary nitrogen atom substitutents include, but are not limited to, hydrogen, $-OH$, $-OR^{aa}$, $-N(R^{cc})_2$, $-CN$, $-C(=O)R^{aa}$, $-C(=O)N(R^{cc})_2$, $-CO_2R^{aa}$, $-SO_2R^{aa}$, $-C(=NR^{bb})R^{aa}$, $-C(=NR^{cc})OR^{aa}$, $-C(=NR^{cc})N(R^{cc})_2$, $-SO_2N(R^{cc})_2$, $-SO_2R^{cc}$, $-SO_2OR^{cc}$, $-SOR^{aa}$, $-C(=S)N(R^{cc})_2$, $-C(=O)SR^{cc}$, $-C(=S)SR^{cc}$, $-P(=O)_2R^{aa}$, $-P(=O)(R^{aa})_2$, $-P(=O)_2N(R^{cc})_2$, $-P(=O)(NR^{cc})_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on a nitrogen atom is an amino protecting group, also referred to herein as a nitrogen protecting group. Amino protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Nitrogen protecting groups such as amide groups (e.g., $-C(=O)R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., $-C(=O)OR^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., $-S(=O)_2R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group. Oxygen protecting groups include, but are not limited to, —$R^{aa}$, —C(=O)$SR^{aa}$, —C(=O)$R^{aa}$ ("acyl"), —$CO_2R^{aa}$, —C(=O)N($R^{bb}$)$_2$, —C(=$NR^{bb}$)$R^{aa}$, —C(=$NR^{bb}$)$OR^{aa}$, —C(=$NR^{bb}$)N($R^{bb}$)$_2$, and —Si($R^{aa}$)$_3$, wherein $R^{aa}$, $R^{bb}$, and $R^{cc}$ are as defined herein. Hydroxyl protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxyl)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxide, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthhyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

DETAILED DESCRIPTION OF CERTAIN EMBODIMENTS OF THE INVENTION

As previously described herein, the present invention provides new labeling reagents for the trapping and detection of reactive metabolites of drug and drug candidates.

Such reagents may be useful in methods for detecting a reactive metabolite in a sample, e.g., wherein the metabolite is present in the sample or is generated from the metabolism of a test compound, and wherein the metabolite and a reagent of Formula (I) or (II) react to form a detectable adduct, e.g., detectable by mass spectrometry. The present invention is further envisioned useful for confirming that a reactive metabolite is not present in a sample, e.g., wherein no adduct is detected.

Thus, in one aspect, provided is a compound of Formula (I), which may be used as a labeling reagent when $R^3$ is hydrogen:

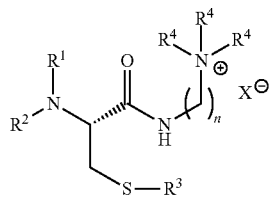

(I)

wherein:

each instance of $R^1$ and $R^2$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=O)$R^A$, —C(=O)O$R^A$, —C(=O)N($R^A$)$_2$, or an amino protecting group, or $R^1$ and $R^2$ are joined to form a substituted or unsubstituted heterocyclic ring;

each instance of $R^A$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a nitrogen protecting group when attached to a nitrogen atom, or two $R^A$ groups are joined to form a substituted or unsubstituted heterocyclic ring;

$R^3$ is hydrogen or a sulfur protecting group;

each instance of $R^4$ is independently substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, or two $R^4$ groups are joined to form a substituted or unsubstituted heterocyclic ring;

n is 1, 2, 3, 4, 5, or 6; and $X^-$ is a counter anion.

Additionally, in another aspect, provided is a compound of Formula (II), which may be used as a labeling reagent when $R^3$ is hydrogen:

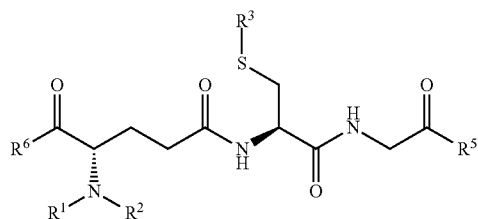

(II)

wherein:

each instance of $R^1$ and $R^2$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=O)$R^A$, —C(=O)O$R^A$, —C(=O)N($R^A$)$_2$, or an amino protecting group, or $R^1$ and $R^2$ are joined to form a substituted or unsubstituted heterocyclic ring;

each instance of $R^A$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a nitrogen protecting group when attached to a nitrogen atom, or two $R^A$ groups are joined to form a substituted or unsubstituted heterocyclic ring;

$R^3$ is hydrogen or a sulfur protecting group;

$R^5$ and $R^6$ are independently selected from —O$R^B$, —N($R^B$)$_2$, and a group of Formula (i):

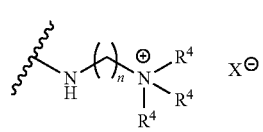

(i)

provided at least one of $R^5$ and $R^6$ is a group of formula (i);

each instance of $R^B$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a nitrogen protecting group when attached to a nitrogen atom, or two $R^B$ groups are joined to form a substituted or unsubstituted heterocyclic ring;

each instance of $R^4$ is independently substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, or two $R^4$ groups are joined to form a substituted or unsubstituted heterocyclic ring;

n is 1, 2, 3, 4, 5, or 6; and $X^-$ is a counter anion.

As generally described above, provided are compounds of Formula (I) or (II), which may be useful, in certain embodiments, as labeling reagents wherein $R^3$ is hydrogen. The present invention also contemplates protected forms of these compounds, e.g., corresponding synthetic intermediates, wherein $R^3$ is a sulfur protecting group.

In certain embodiments, $R^1$ is hydrogen. In certain embodiments, $R^1$ is substituted or unsubstituted alkyl, e.g., —$CH_3$, or substituted or unsubstituted aralkyl. In certain embodiments, $R^1$ is substituted or unsubstituted alkenyl, e.g., allyl. In certain embodiments, $R^1$ is substituted or unsubstituted alkynyl, e.g., propynyl. In certain embodiments, $R^1$ is substituted or unsubstituted carbocyclyl. In certain embodiments, $R^1$ is substituted or unsubstituted heterocyclyl. In certain embodiments, $R^1$ is substituted or unsubstituted aryl. In certain embodiments, $R^1$ is substituted or unsubstituted heteroaryl. In certain embodiments, $R^1$ is —$C(=O)R^A$. In certain embodiments, R is —$C(=O)OR^A$. In certain embodiments, R is —$C(=O)N(R^A)_2$. In certain embodiments, $R^1$ is an amino protecting group.

In certain embodiments, $R^2$ is hydrogen. In certain embodiments, $R^2$ is substituted or unsubstituted alkyl, e.g., —$CH_3$, or substituted or unsubstituted aralkyl. In certain embodiments, $R^2$ is substituted or unsubstituted alkenyl, e.g., allyl. In certain embodiments, $R^2$ is substituted or unsubstituted alkynyl, e.g., propynyl. In certain embodiments, $R^2$ is substituted or unsubstituted carbocyclyl. In certain embodiments, $R^2$ is substituted or unsubstituted heterocyclyl. In certain embodiments, $R^2$ is substituted or unsubstituted aryl. In certain embodiments, $R^2$ is substituted or unsubstituted heteroaryl. In certain embodiments, $R^2$ is —$C(=O)R^A$. In certain embodiments, $R^2$ is —$C(=O)OR^A$. In certain embodiments, $R^2$ is —$C(=O)N(R^A)_2$. In certain embodiments, $R^2$ is an amino protecting group.

In certain embodiments, $R^1$ and $R^2$ are joined to form a substituted or unsubstituted heterocyclic ring, e.g., for example, a substituted or unsubstituted pyrrolidinyl, piperidinyl, piperazinyl, or morpholinyl ring.

Alternatively, $R^1$ and $R^2$ may be joined to form a substituted or unsubstituted heteroaryl ring, e.g., a 5- to 6-membered heteroaryl ring.

In certain embodiments, $R^1$ is hydrogen, and $R^2$ is hydrogen, —$C(=O)R^A$, —$C(=O)OR^A$, —$C(=O)N(R^A)_2$, or an amino protecting group. In certain embodiments, $R^1$ is hydrogen and $R^2$ is —$C(=O)R^A$, —$C(=O)OR^A$, or —$C(=O)N(R^A)_2$. In certain embodiments, $R^1$ is hydrogen and $R^2$ is —$C(=O)R^A$. In certain embodiments, $R^1$ is hydrogen and $R^2$ is —$C(=O)OR^A$. In certain embodiments, $R^1$ is hydrogen and $R^2$ is —$C(=O)N(R^A)_2$. In certain embodiments, $R^1$ is hydrogen and $R^2$ is hydrogen.

In certain embodiments, at least one instance of $R^A$ is hydrogen. In certain embodiments, at least one instance of $R^A$ is substituted or unsubstituted alkyl, e.g., —$CH_3$, or substituted or unsubstituted aralkyl. In certain embodiments, at least one instance of $R^A$ is substituted or unsubstituted alkenyl, e.g., allyl. In certain embodiments, at least one instance of $R^A$ is substituted or unsubstituted alkynyl, e.g., propynyl. In certain embodiments, at least one instance of $R^A$ is substituted or unsubstituted carbocyclyl. In certain embodiments, at least one instance of $R^A$ is substituted or unsubstituted heterocyclyl. In certain embodiments, at least one instance of $R^A$ is substituted or unsubstituted aryl. In certain embodiments, at least one instance of $R^A$ is substituted or unsubstituted heteroaryl. In certain embodiments, $R^A$ is an oxygen protecting group. In certain embodiments, at least one instance of $R^A$ is a nitrogen protecting group.

In certain embodiments, wherein two $R^A$ groups are attached to an N atom, the two $R^A$ groups are joined to form a substituted or unsubstituted heterocyclic ring, e.g., for example, a substituted or unsubstituted pyrrolidinyl, piperidinyl, piperazinyl, or morpholinyl ring.

Alternatively, two $R^A$ groups may be joined to form a substituted or unsubstituted heteroaryl ring, e.g., a 5- to 6-membered heteroaryl ring.

In certain embodiments, at least one $R^A$ is —$CH_3$, e.g., to provide a group of formula —$C(=O)CH_3$, —$C(=O)OCH_3$, or —$C(=O)NHCH_3$. In certain embodiments, $R^1$ is hydrogen and $R^2$ is —$C(=O)CH_3$, —$C(=O)OCH_3$, or —$C(=O)NHCH_3$. In certain embodiments, $R^1$ is hydrogen and $R^2$ is —$C(=O)CH_3$. In certain embodiments, $R^1$ is hydrogen and $R^2$ is —$C(=O)OCH_3$. In certain embodiments, $R^1$ is hydrogen and $R^2$ is —$C(=O)NHCH_3$.

In certain embodiments, at least one $R^A$ is substituted or unsubstituted aryl or substituted or unsubstituted aralkyl. In this instance, in certain embodiments, at least one $R^A$ is a group of Formula (a):

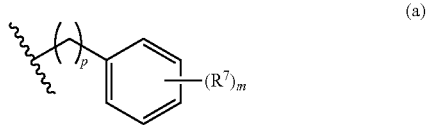

wherein:
p is 0, to provide a substituted or unsubstituted aryl; or
p is 1 or 2, to provide a substituted or unsubstituted aralkyl;
m is 1, 2, 3, 4, or 5; and
each instance of $R^7$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl.

For example, in certain embodiments, $R^1$ is hydrogen and $R^2$ is —$C(=O)R^A$, —$C(=O)OR^A$, or —$C(=O)N(R^A)_2$, wherein $R^A$ is a group of Formula (a). In certain embodiments, $R^1$ is hydrogen and $R^2$ is —$C(=O)R^A$, wherein $R^A$ is a group of Formula (a). In certain embodiments, $R^1$ is hydrogen and $R^2$ is —$C(=O)OR^A$, wherein $R^A$ is a group of Formula (a). In certain embodiments, $R^1$ is hydrogen and $R^2$ is —$C(=O)NH(R^A)$, wherein $R^A$ is a group of Formula (a).

In certain embodiments, p is 0. In certain embodiments, p is 1 or 2. In certain embodiments, p is 1. In certain embodiments, p is 2.

In certain embodiments, each instance of $R^7$ is independently halogen, e.g., selected from the group consisting of fluoro, bromo, iodo, and chloro. In certain embodiments, each instance of $R^7$ is independently selected from the group consisting of bromo and fluoro. In certain embodiments, each instance of $R^7$ is bromo. In certain embodiments, each instance of $R^7$ is fluoro.

Various mono-, di-, tri-, and tetra-substituted Formula (a) groups are contemplated. For example, in certain embodiments, wherein m is 1, the group of Formula (a) is an ortho, meta, or para substituted group of the formulae:

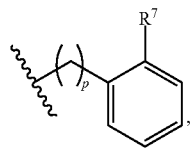

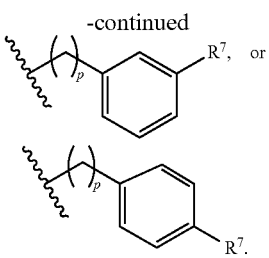

In certain embodiments, wherein m is 2, the group of Formula (a) is a disubstituted group of any one of the Formula:

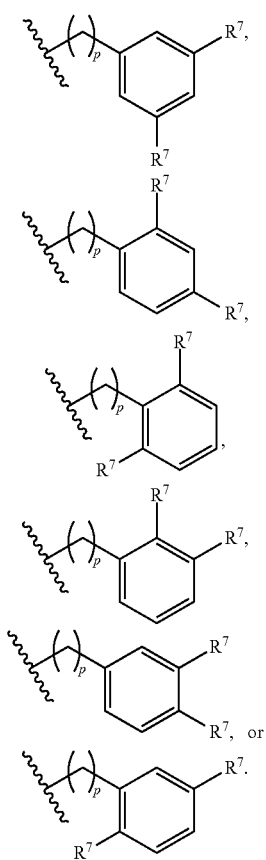

In certain embodiments, wherein m is 3, the group of Formula (a) is a trisubstituted group of any one of the Formula:

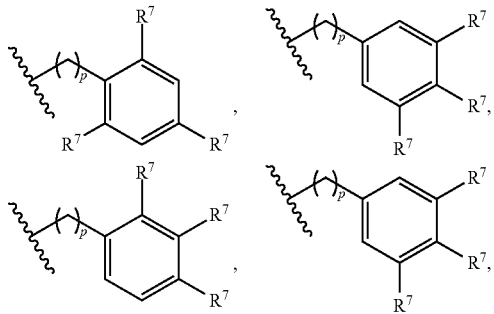

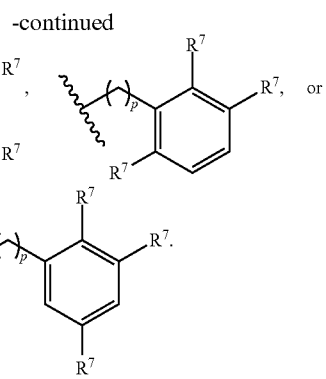

In certain embodiments, wherein m is 4, the group of Formula (a) is a tetrasubstituted group of any one of the Formula:

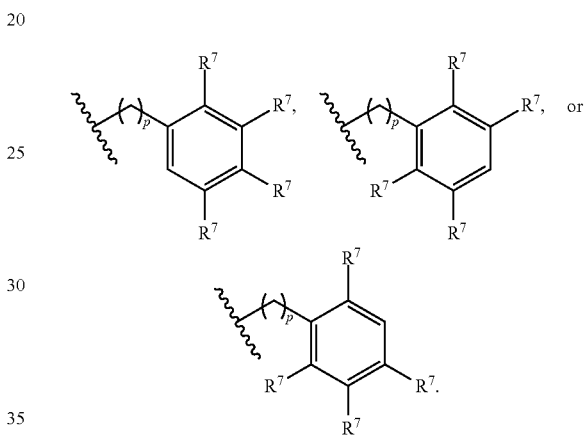

In certain embodiments, wherein m is 5, the group of Formula (a) is a pentasubstituted group:

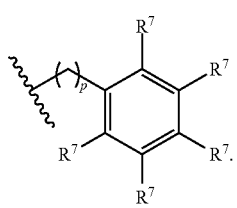

In certain embodiments, m is 1 and $R^7$ is bromo. In certain embodiments, $R^7$ is an ortho-bromo group.

In certain embodiments, m is 5 and $R^7$ is fluoro.

In certain embodiments, at least one instance of $R^4$ is substituted or unsubstituted alkyl, e.g., —CH$_3$, substituted or unsubstituted aralkyl. In certain embodiments, at least one instance of $R^4$ is substituted or unsubstituted alkenyl, e.g., allyl. In certain embodiments, at least one instance of $R^4$ is substituted or unsubstituted alkynyl, e.g., propynyl. In certain embodiments, at least one instance of $R^4$ is substituted or unsubstituted carbocyclyl. In certain embodiments, at least one instance of $R^4$ is substituted or unsubstituted heterocyclyl. In certain embodiments, at least one instance of $R^4$ is substituted or unsubstituted aryl. In certain embodiments, at least one instance of $R^4$ is substituted or unsubstituted heteroaryl. In certain embodiments, at least one instance of $R^4$ is an amino protecting group.

In certain embodiments, two instances of $R^4$ is the same. In certain embodiments, each instance of $R^4$ is the same. In certain embodiments, each instance of $R^4$ is different.

In certain embodiments, at least one instance of $R^4$ is substituted or unsubstituted alkyl, e.g., substituted or unsubstituted $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, or $C_{5-6}$ alkyl. In certain embodiments, each instance of $R^4$ is substituted or unsubstituted $C_1$ alkyl, e.g., —$CH_3$. In certain embodiments, each instance of $R^4$ is —$CH_3$.

In certain embodiments, two $R^4$ groups are joined to form a substituted or unsubstituted heterocyclic ring, e.g., for example, a substituted or unsubstituted pyrrolidinyl, piperidinyl, piperazinyl, or morpholinyl ring.

Alternatively, one $R^4$ group is absent, and the other two $R^4$ groups may be joined to form a substituted or unsubstituted heteroaryl ring, e.g., a 5- to 6-membered heteroaryl ring.

In certain embodiments, n is 1. In certain embodiments, n is 2, In certain embodiments, n is 3. In certain embodiments, n is 4. In certain embodiments, n is 5. In certain embodiments, n is or 6.

As used herein, a "counter anion" or "anion" is a negatively charged group associated with the positively charged quarternary amine. Exemplary counteranions include halide ions (e.g., fluoride, chloride, bromide, iodide), $NO_3^-$, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate), and carboxylate ions (e.g., acetate, ethanoate, propanoate, benzoate, glycerate, lactate, tartrate, glycolate). In certain embodiments, X is a halide counteranion, e.g., a chloride counteranion.

As generally defined above for Formula (II), $R^5$ and $R^6$ are independently selected from —$OR^B$, —$N(R^B)_2$, and a group of Formula (i):

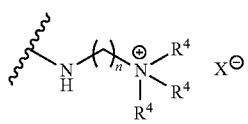

provided at least one of $R^5$ and $R^6$ is a group of Formula (i), wherein $X^-$, $R^4$ and n are as defined herein.

In certain embodiments, $R^5$ is —$OR^B$ and $R^6$ is a group of Formula (i).

In certain embodiments, $R^5$ is —$N(R^B)_2$ and $R^6$ is a group of Formula (i).

In certain embodiments, $R^6$ is —$OR^B$ and $R^5$ is a group of Formula (i).

In certain embodiments, $R^6$ is —$N(R^B)_2$ and $R^5$ is a group of Formula (i).

In certain embodiments, at least one instance of $R^B$ is hydrogen. In certain embodiments, at least one instance of $R^B$ is substituted or unsubstituted alkyl, e.g., —$CH_3$, substituted or unsubstituted aralkyl. In certain embodiments, at least one instance of $R^B$ is substituted or unsubstituted alkenyl, e.g., allyl. In certain embodiments, at least one instance of $R^B$ is substituted or unsubstituted alkynyl, e.g., propynyl. In certain embodiments, at least one instance of $R^B$ is substituted or unsubstituted carbocyclyl. In certain embodiments, at least one instance of $R^B$ is substituted or unsubstituted heterocyclyl. In certain embodiments, at least one instance of $R^B$ is substituted or unsubstituted aryl. In certain embodiments, at least one instance of $R^B$ is substituted or unsubstituted heteroaryl. In certain embodiments, $R^B$ is an oxygen protecting group. In certain embodiments, at least one instance of $R^B$ is a nitrogen protecting group.

In certain embodiments, wherein two $R^B$ groups are attached to an N atom, the two $R^B$ groups are joined to form a substituted or unsubstituted heterocyclic ring, e.g., for example, a substituted or unsubstituted pyrrolidinyl, piperidinyl, piperazinyl, or morpholinyl ring.

Alternatively, two $R^B$ groups may be joined to form a substituted or unsubstituted heteroaryl ring, e.g., a 5- to 6-membered heteroaryl ring.

In certain embodiments, at least one $R^B$ is substituted or unsubstituted aryl or substituted or unsubstituted aralkyl. In this instance, in certain embodiments, at least one $R^B$ is a group of Formula (a), as defined herein.

As would be appreciated by one of skill in the art, various combinations of $R^1$, $R^2$, $R^3$, $R^4$, $R^5$, $R^6$, $R^A$, $R^B$, X and n as described herein are possible and contemplated by the present invention. The invention is not limited by the particular formulae and conditions explicitly described.

In certain embodiments, wherein $R^3$ is hydrogen, the compound of Formula (I) is Formula (I-a):

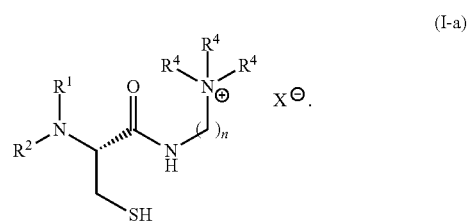

In certain embodiments, wherein n is 2, the compound of Formula (I) is Formula (I-b):

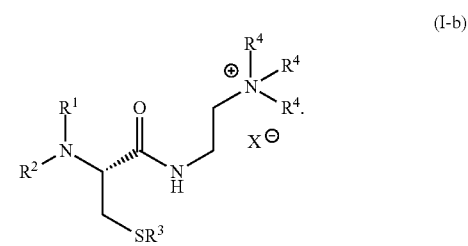

In certain embodiments of Formula (I-b), $R^3$ is hydrogen.

In certain embodiments, wherein n is 2, and each instance of $R^4$ is —$CH_3$, the compound of Formula (I) is Formula (I-c):

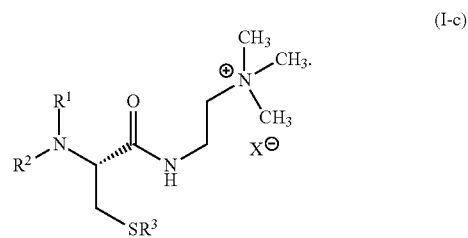

In certain embodiments of Formula (I-c), $R^3$ is hydrogen.

Exemplary compounds of Formula (I) include, but are not limited to:

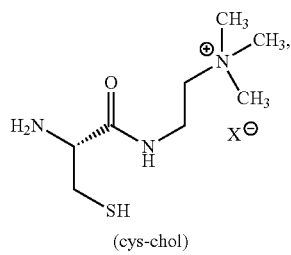
(cys-chol)

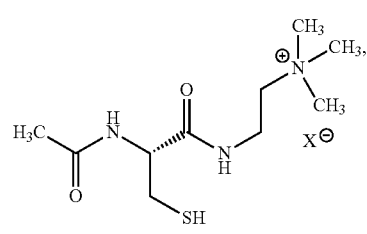

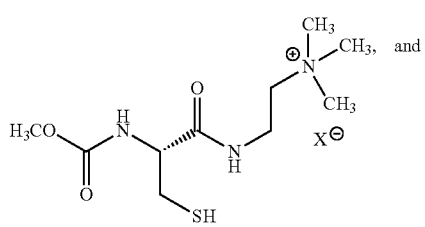
and

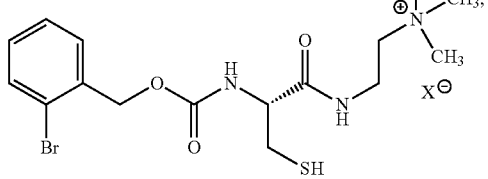

wherein $X^-$ is a counteranion. In certain embodiments $X^-$ is a chloride counteranion.

In certain embodiments, wherein $R^3$ is hydrogen, the compound of Formula (II) is Formula (II-a):

(II-a)

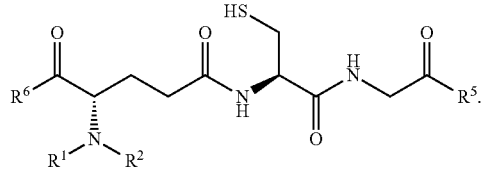

In certain embodiments, wherein $R^5$ is a group of Formula (i) and $R^6$ is $-OR^B$, the compound of Formula (II) is Formula (II-b):

(II-b)

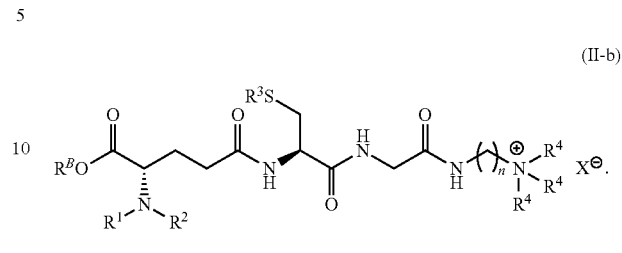

In certain embodiments of Formula (II-b), $R^3$ is hydrogen.

In certain embodiments, wherein n is 2, $R^5$ is a group of Formula (i), and $R^6$ is $-OR^B$, the compound of Formula (II) is Formula (II-c):

(II-c)

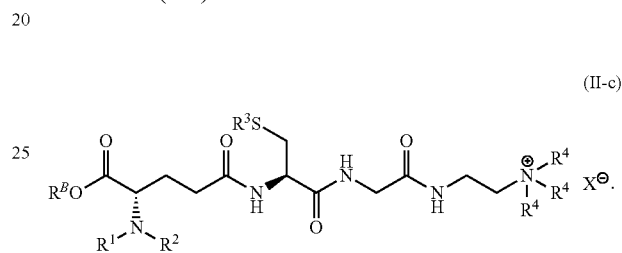

In certain embodiments of Formula (II-c), $R^3$ is hydrogen.

In certain embodiments, wherein n is 2, each instance of $R^4$ is $-CH_3$, $R^5$ is a group of Formula (i), and $R^6$ is $-OR^B$, the compound of Formula (II) is Formula (II-d):

(II-d)

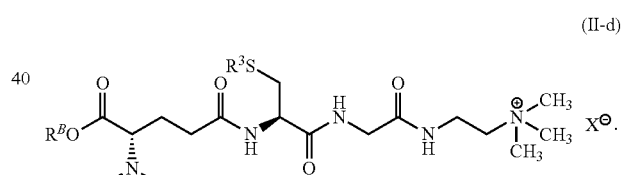

In certain embodiments of Formula (II-d), $R^3$ is hydrogen.

In certain embodiments, wherein $R^6$ is a group of Formula (i), and $R^5$ is $-OR^B$, the compound of Formula (II) is Formula (II-e):

(II-e)

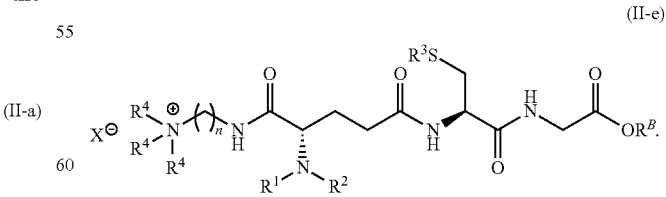

In certain embodiments of Formula (II-e), $R^3$ is hydrogen.

In certain embodiments, wherein n is 2, $R^6$ is a group of Formula (i), and $R^5$ is $-OR^B$, the compound of Formula (II) is Formula (II-f):

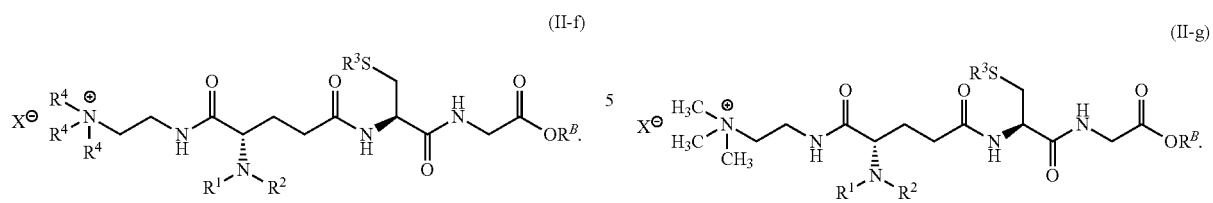
In certain embodiments of Formula (II-f), R³ is hydrogen.
In certain embodiments, wherein n is 2, each instance of R⁴ is —CH₃, R⁶ is a group of Formula (i), and R⁵ is —OR$^B$, the compound of Formula (II) is Formula (II-g):
In certain embodiments of Formula (II-f), R³ is hydrogen.
Exemplary compounds of Formula (II) include, but are not limited to:
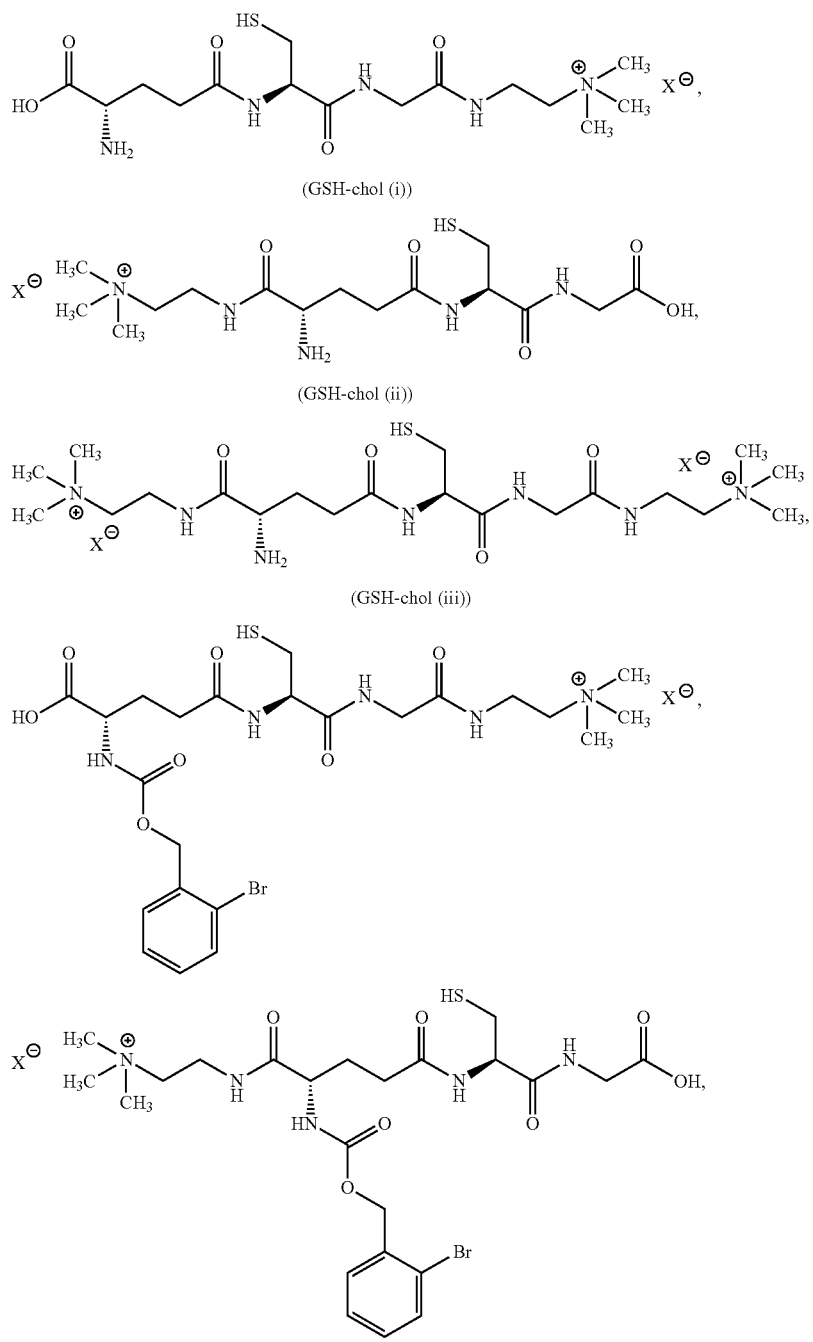
(GSH-chol (i))
(GSH-chol (ii))
(GSH-chol (iii))

-continued
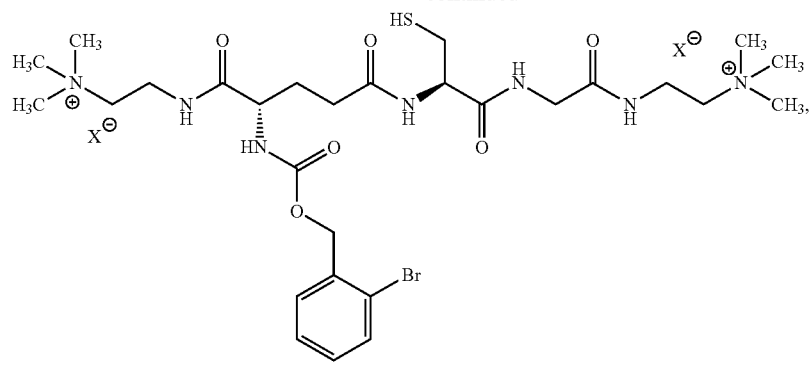
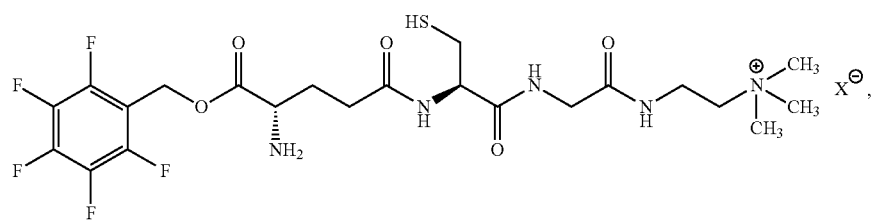
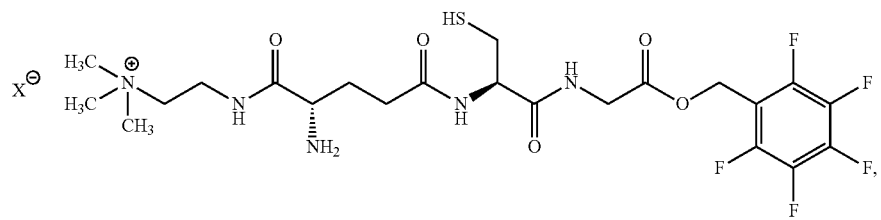
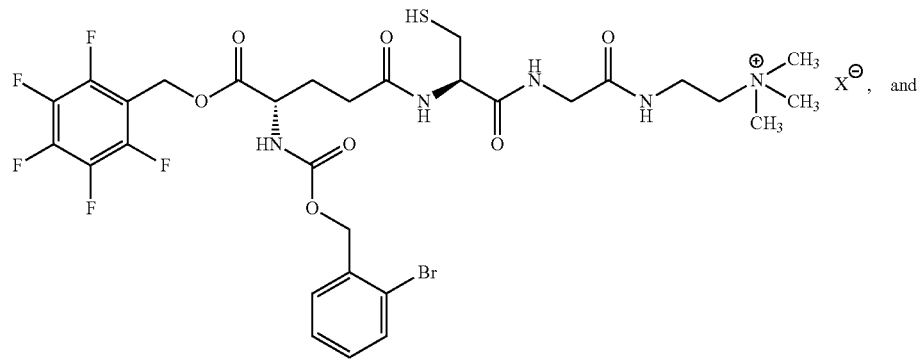, and
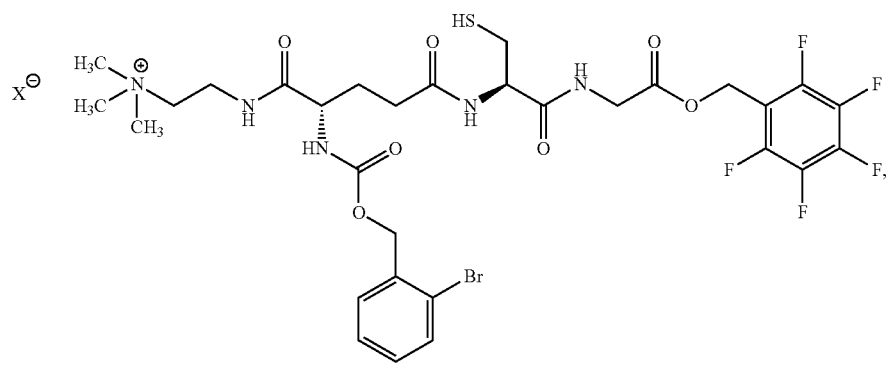

wherein X⁻ is a counteranion. In certain embodiments X⁻ is a chloride counteranion.

Screening Methods and Kits

In one aspect, the present invention provides a method for detecting a metabolite in a sample comprising contacting a sample comprising a metabolite and a reagent of Formula (I) or (II):

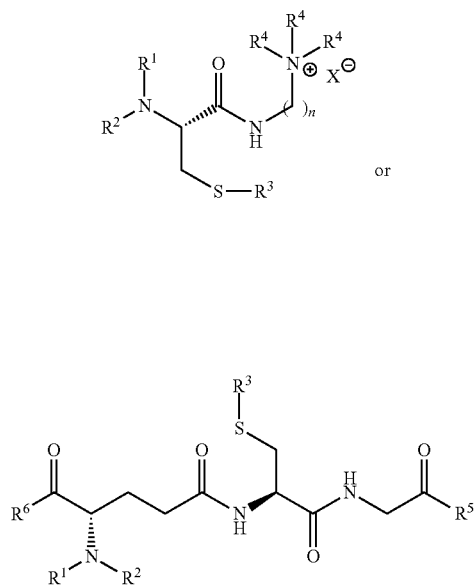

wherein $R^1$, $R^2$, $R^4$, $R^5$, $R^6$, X and n are as defined herein, and $R^3$ is hydrogen, wherein the metabolite and the reagent of Formula (I) or (II) react to form an adduct; and detecting the adduct, e.g., by mass spectrometry.

In certain embodiments, the sample comprises an enzyme system. In certain embodiments, the sample comprises a test compound. In certain embodiments, the step of contacting further comprises contacting the sample comprising a test compound and the enzyme system, wherein the metabolite is generated from metabolism by the enzyme system with the test compound. In certain embodiments, the enzyme system is a P450 microsomal enzyme system. The P450 microsomal enzyme systems of the body, e.g., typically found in the liver, help "detoxify" the human body. Thus, when a test compound, such as a drug or drug candidate, is introduced into the body, a P450 microsomal enzyme system may metabolize the drug or drug candidate. The by-product of that process may be a reactive metabolite. In certain embodiments, the P450 microsomal enzyme system is selected the group consisting of microsomes, S9 fractions, and P450 enzymes. In certain embodiments, the microsomes are mammalian liver microsomes, e.g., human liver microsomes. In certain embodiments, the S9 fraction is mammalian S9 fraction, e.g., human liver S9 fraction. See also U.S. Pat. Nos. 5,478,723 and 5,891,696 which describe various P450 microsomal enzyme systems.

In another aspect, the screening method is a method for detecting a metabolite in a sample, the method comprising contacting a test compound, an enzyme system, and a compound of Formula (I) or (II):

wherein $R^1$, $R^2$, $R^4$, $R^5$, $R^6$, X and n are as defined herein, and $R^3$ is hydrogen, wherein the test compound is metabolized by the enzyme system to provide a metabolite; and wherein the metabolite reacts with a compound of Formula (I) or (II) to form an adduct; and detecting the adduct, e.g., by mass spectrometry.

In certain embodiments, the concentration of the test compound is between about 1 nM and about 1 mM, for example between about 100 nM and 100 uM. In certain embodiments, the concentration of the test compound is about 10 uM. However, it should be appreciated that other concentrations may be used.

In certain embodiments, the concentration of the compound of Formula (I) or (II) is between about 1 nM and about 1 mM, for example between about 100 nM and 100 uM. In certain embodiments, the concentration of the compound of Formula (I) or (II) is about 5 uM. However, it should be appreciated that other concentrations may be used.

In certain embodiments, concentration of the metabolite is between about 1 nM and about 1 mM, for example between about 100 nM and 100 uM. However, it should be appreciated that other concentrations may be used.

In certain embodiments, the test compound, an enzyme system, and a compound of Formula (I) or (II) are provided in a solution, e.g., an aqueous solution. In certain embodiments, the aqueous solution comprises water, an organic solvent, or a mixture thereof. In certain embodiments, the aqueous solution is buffered, e.g., for example, buffered with potassium phosphate buffer. In certain embodiments, the pH of the aqueous solution is about 7.0 to about 7.6, e.g., about 7.4.

In certain embodiments, the contacting step comprises pre-incubating for about 1 to about 10 minutes, inclusive, prior to addition of a NADPH-generating system or NADPH. In certain embodiments, adduct formation is initiated by addition of a NADPH-generating system or NADPH. In certain embodiments, the pre-incubating step is about 3 to about 5 minutes, inclusive. In certain embodiments, the pre-incubating step is about 3 minutes.

In certain embodiments, after addition of the NADPH-generating system or NADPH, the mixture is further incubated for about 30 minutes to about 2 hours. In certain embodiments, the mixture is further incubated for about 1 hour.

In certain embodiments, the temperature of the solution during the incubating step is about 30° C. to about 40° C., inclusive. In certain embodiments, the temperature of the solution during the incubating step is about 37° C.

In certain embodiments, the reaction is quenched prior to the detecting step. In certain embodiments, the reaction is quenched with acid. In certain embodiments, the acid is an inorganic acid, e.g., HCl. In certain embodiments, the acid is an organic acid, e.g., formic acid. In certain embodiments, the reaction is quenched with 0.1% formic acid in an organic solvent, e.g., acetonitrile. In certain embodiments, after quenching, the reaction is centerfuged, and the sample is tested directly without further purification or additional work-up.

In certain embodiments, the adduct is detected by mass spectrometry (MS). As used herein, "detecting" encompasses identifying the prescence of the adduct directly as well as indirectly, such as by inferring the presence of the adduct from the identification of a characteristic moiety or fragmentation product of the adduct, e.g., when the adduct is further processed (e.g., for example, by the collision induced dissociation produced in a triple quadropole mass spectrometer). In certain embodiments, the mass spectrometry is tandem mass spectrometry (MS/MS). In certain embodiments, the mass spectrometry is ESI coupled with tandem mass spectrometry (ESI-MS/MS). In certain embodiments, the adduct is detected using a combination of liquid chromatography coupled to mass spectrometry. In certain embodiments, the liquid chromatography is high pressure liquid chromatography (HPLC). In certain embodiments, the liquid chromatography is ultra high pressure liquid chromatography (UPLC or UHPLC).

In certain embodiments, the methods as described herein are methods for detecting low levels of already known metabolites. In certain embodiments, the methods as described herein are methods of identifying new metabolites. In certain embodiments, the methods as described herein are methods of improving the resolution or confidence of metabolite detection.

Further provided are kits for performing the assays as described herein. The kits may include, are not limited to, one or more enzyme systems, standard test compounds, vials and/or containers, solutions, one or more compounds of Formula (I) or (II), and instructions for use.

Covalent Adduct Formation

In vivo, glutathione (GSH) covalently binds through its nucleophilic thiol group with the reactive electrophilic moieties of reactive species to form stable S-substituted conjugates, which are excreted, thereby providing a natural mechanism for preventing such reactive species from binding with vital cellular constituents. The screening assays as described herein are contemplated to mimic the in vivo behavior of glutathione. The reaction of the free thiol group of a compound of Formula (I) or (II) with one or more reactive metabolites present in the sample to form a covalent adduct is a chemical reaction well-known in the art, see, e.g., Fluharty, *Biochemistry of the Thiol Group, In the Chemistry of the Thiol Group*, ed. S. Patai, Wiley, New York, 1974; Clark, *Chemical Reviews* (1980) 80:429-452; Fujita et al., *Bioorganic Chemistry* (1977) 6:287-309; and Perlmutter, *Conjugated Addition Reactions in Organic Synthesis*, Pergamon, Oxford, 1992. For example, the thiol group may react with Michael acceptors or dienes by 1,4-addition, or with activated carbonyl groups or olefinic groups by 1,2-addition, to form covalent adducts.

Thus, in another aspect, provided is a covalent adduct of the metabolite and the compound of Formula (I) or (II):

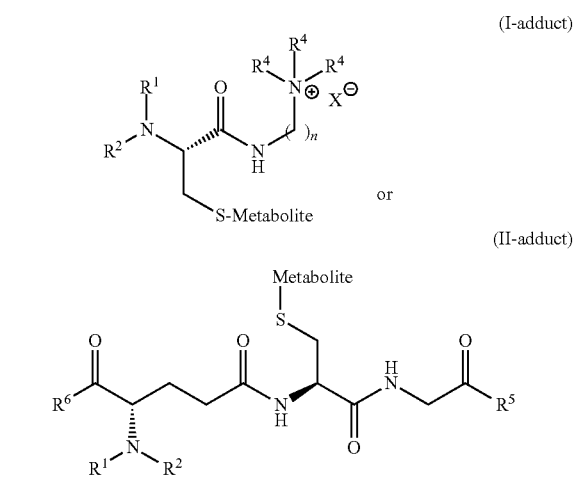

wherein $R^1$, $R^2$, $R^4$, $R^5$, $R^6$, X and n are as defined herein, and the Metabolite prior to formation of the adduct is a metabolite of any test compound, e.g., a drug or drug candidate, which comprises an electrophilic reactive moiety, e.g., a Michael acceptor, diene, olefin, or activated carbonyl group, capable of covalent conjugation with a free thiol group to form the adduct.

Exemplary drugs to be tested and which may, upon metabolism, form a covalent adduct with the thiol reagents described herein include, but are not limited to, any drug approved by the U.S. Food and Drug Administration as provided in the Code of Federal Regulations (CFR). Drug candidates are compounds not yet approved, but are under development for biological testing on a subject, e.g., a human (i.e., a male or female of any age group, e.g., a pediatric subject (e.g, infant, child, adolescent) or adult subject (e.g., young adult, middle-aged adult or senior adult)) and/or other non-human animals, for example mammals [e.g., primates (e.g., cynomolgus monkeys, rhesus monkeys); and commercially relevant mammals such as mice, rats, hampsters, cattle, pigs, horses, sheep, goats, cats, and/or dogs] and birds (e.g., commercially relevant birds such as chickens, ducks, geese, and/or turkeys).

It should be appreciated that in some embodiments the detection of an adduct in a sample can be indicative of a reactive metabolite that may be undesirable (e.g., potentially toxic to a subject). In some embodiments, if an adduct is detected (e.g., for a drug candidate) further analysis of the adduct can be useful to identify the reactive metabolite. In some embodiments, the presence of a particular reactive metabolite and/or undesirable levels or one or more reactive metabolites can lead to a drug or drug candidate not being selected for therapeutic use. In some embodiments, if a particular reactive metabolite and/or undesirable levels or one or more reactive metabolites are detected in a sample, a drug candidate can be modified and/or one or more synthetic steps for the drug or drug candidate can be modified to avoid or reduce the level of one or more reactive metabolites.

Examples

These and other aspects of the present invention will be further appreciated upon consideration of the following Examples, which are intended to illustrate certain particular embodiments of the invention but are not intended to limit its scope, as defined by the claims.

Synthesis of Cholamine-Modified Cysteine (Cys-Chol)

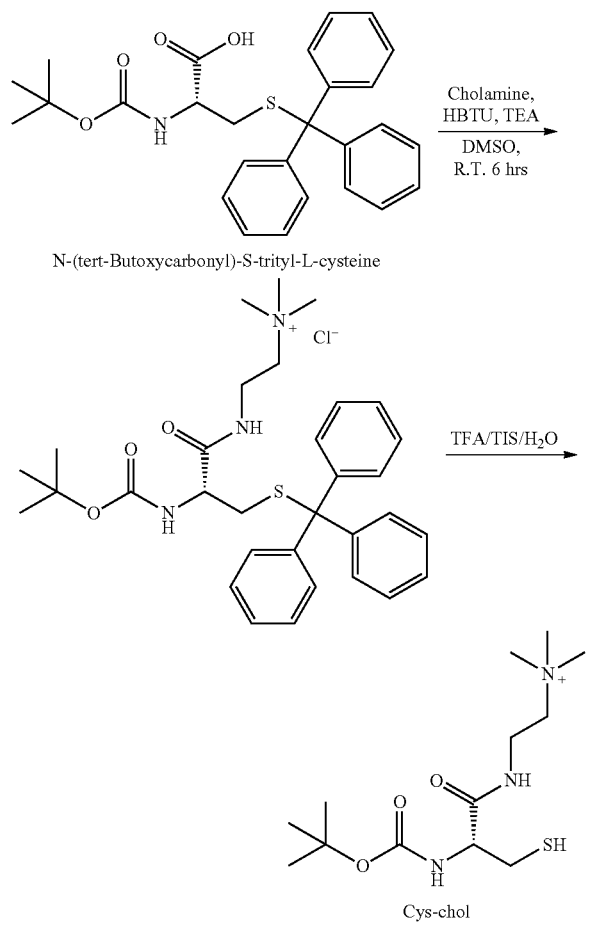

Protected cysteine was coupled to cholamine using standard peptide coupling conditions. Deprotection afforded the final product, cys-chol, which was purified by SPE with WCX cartridge. Purity of the final product was confirmed by LC-MS.

In Vitro Liver Microsomal Incubations

Pooled human liver microsomes (HLM) were obtained. 320 uL of HLM master mix (HLM, 20 mg/mL; 1 mg/mL final concentration) was added to an incubation tube containing cysteine or cys-chol in phosphate buffer (0.1 M final concentration, pH 7.4), followed by addition of 40 uL of 100 uM of test compound in water (10 uM final concentration). Following preincubation at 37° C. for 3 minutes, the reaction was initiated by the addition of 40 uL of a 10 mM NADPH-generating system, 6.2 mM DL-isocitric acid, and 0.5 units/mL isocitric dehydrogenase). The final incubation volume was 250 uL. Samples without substrate or NADPH added were used as negative controls. After 60 minutes of incubation at 37° C. and 400 rpm, 400 uL of acetonitrile with 0.1% formic acid were added to the incubations, which were then centerfuged (max rpm, 5 min). The supernatant (200 uL) was transferred to a 96 well plate directly for LC-MS, without further evaporation steps.

Results

Liquid chromatography and Electrosprapy Ionization (ESI)-Tandem Mass Spectrometry were employed. Metabolites from nine tested drugs with cysteine or cys-chol as the trapping reagents were analyzed by UPLC-LTQ Orbitrap or UPLC-AB SCIEX 5600. See Table 1. From these experiments, it was determined that cys-chol trapping is more sensitive than cysteine trapping. See Table 2.

TABLE 1

| Drug | Cysteine adduct | Theoretical MH+ | Detected in Orbitrap | Detected in AB 5600 | Cys-chol adduct | Theoretical MH+ | Detected in Orbitrap | Detected in AB 5600 |
|---|---|---|---|---|---|---|---|---|
| Atorvastatin | Ator + Cys + O—2H | 694.2593 | ND | ND | Ator + Chol + O—2H | 778.3644 | 778.3627 | 778.3636 |
| Bosentan | Bos + Cys-CH2 | 657.1796 | ND | ND | Bos + Chol-CH2 | 741.2847 | 741.2840 | 741.2867 |
| Carbamazepine | CMZ + Cys-2H | 356.1063 | ND | 356.1057 | CMZ + Chol-2H | 440.2115 | 440.2101 | 440.2125 |
| | CMZ + Cys + O | 374.1169 | ND | ND | CMZ + Chol + O | 458.2220 | ND | 458.2224 |
| Clozapine | Clo + Cys-2H | 446.1412 | 446.1400 | 446.1410 | Clo + Chol-2H | 530.2463 | 530.2444 | 530.2460 |
| | Clo + Cys-CH2 | 432.1255 | ND | 432.1256 | Clo + Chol-CH2 | 516.2307 | ND | 516.2305 |
| | Clo + Cys-Cl | 416.1751 | ND | ND | Clo + Chol-HCl | 496.2853 | ND | 496.2849 |
| | Clo + Cys + O | 464.1518 | ND | 464.1523 | Clo + Chol + O | 548.2569 | ND | 548.2553 |
| | Clo + Cys + O—2H | 462.1361 | 462.1344 | 462.1366 | Clo + Chol + O—2H | 546.2412 | 546.2400 | 546.2409 |
| Diclofenac | Dic + Cys-2H | 415.0281 | 415.0258 | 415.0289 | Dic + Chol-2H | 499.1332 | 499.1317 | 499.1345 |
| | Dic + Cys + O—2H | 431.023 | ND | 431.0232 | Dic + Chol + O—2H | 515.1281 | 515.1270 | 515.1273 |
| | Dic + Cys + O—Cl | 397.0619 | 397.0606 | 397.0619 | Dic + Chol + O—HCl | 481.1671 | 481.1659 | 481.1667 |
| Suprofen | Sup + Cys | 382.0777 | ND | ND | Sup + Chol | 466.1829 | 466.1809 | 466.1843 |
| | Sup + Cys-2H | 380.0621 | 380.0622 | 380.0604 | Sup + Chol-2H | 464.1672 | 464.1658 | 464.1676 |
| Troglitazone | Trog + Cys-2H | 561.1724 | ND | ND | Trog + Chol-2H | 645.2775 | 645.2751 | 645.2758 |
| | Trog + Cys + O | 579.1829 | ND | ND | Trog + Chol + O | 663.2881 | ND | 663.2853 |
| | Trog + Cys + O—2H | 577.1673 | ND | ND | Trog + Chol + O—2H | 661.2724 | 661.2706 | 661.2706 |
| Compound A | ComA + Cys-2H | 622.1621 | 622.1621 | 622.1644 | ComA + Cys-2H | 706.2672 | 706.2654 | 706.2667 |
| | ComA + Cys + O—2H | 638.157 | ND | 638.1566 | ComA + Cys + O—2H | 722.2621 | ND | 722.2628 |
| Compound B | ComB + Cys-2H | 703.2199 | 703.2175 | 703.2159 | ComB + Cys-2H | 787.3251 | 787.3241 | 787.3233 |
| | ComB + Cys + O—2H | 719.2149 | 719.2125 | 719.2150 | ComB + Cys + O—2H | 803.3200 | 803.3194 | 803.3169 |

TABLE 2

Number of metabolites found in nine drugs

|  | Cysteine trapping (cys) | Cys-chol trapping |
|---|---|---|
| Orbitrap | 8 | 15 |
| AB5600 | 13 | 21 |

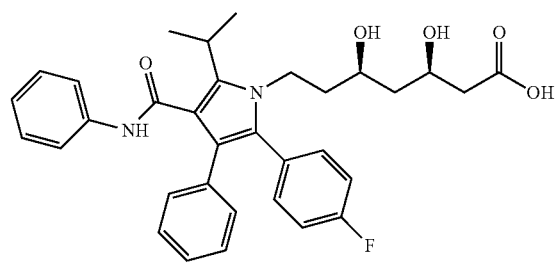

atorvastatin

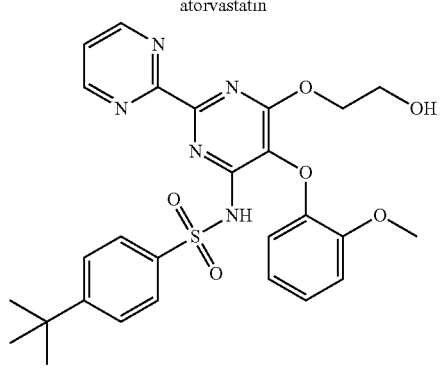

Bosentan

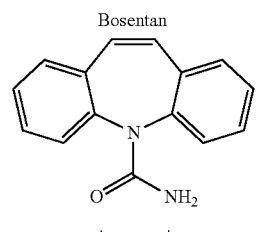

carbamazepine

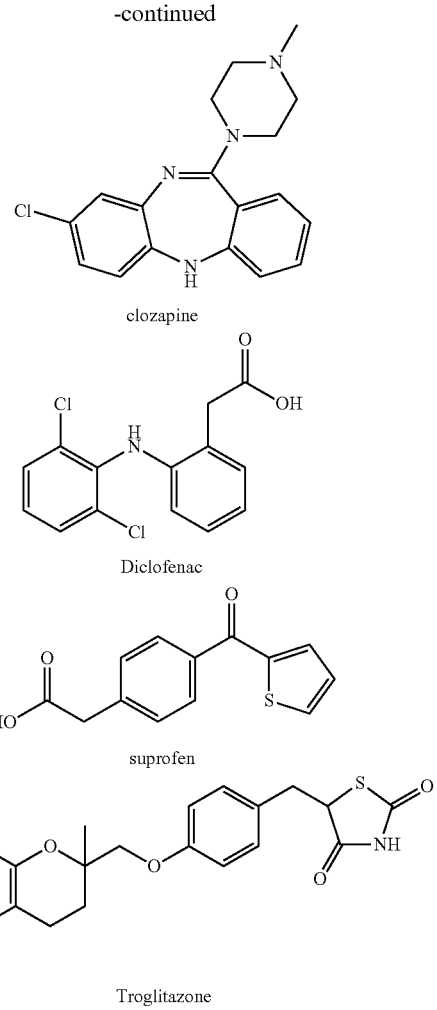

clozapine

Diclofenac suprofen

Troglitazone

Sensitivity Comparison of Three Trapping Reagents

Figure 1B:
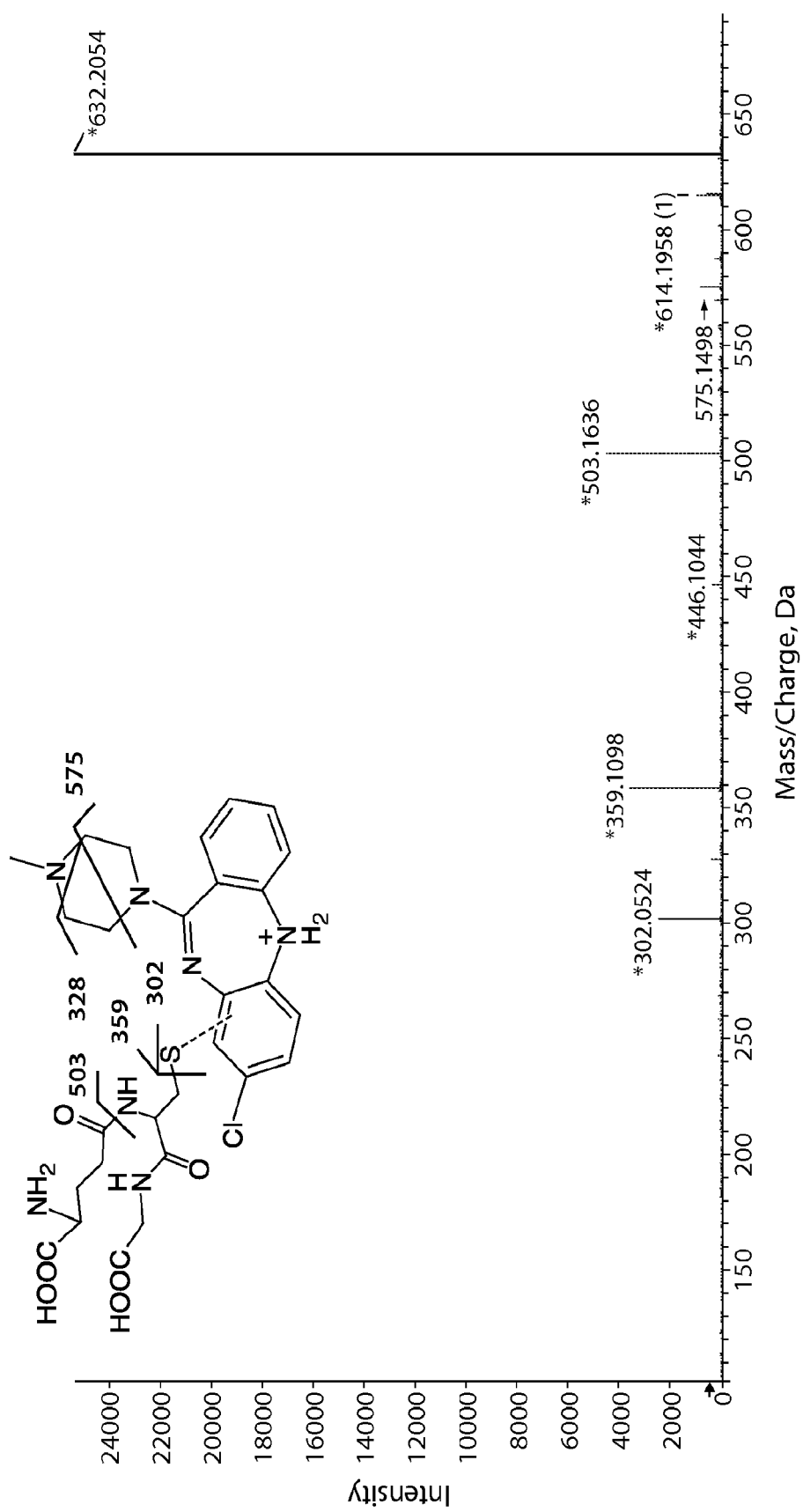
Figure 2A:
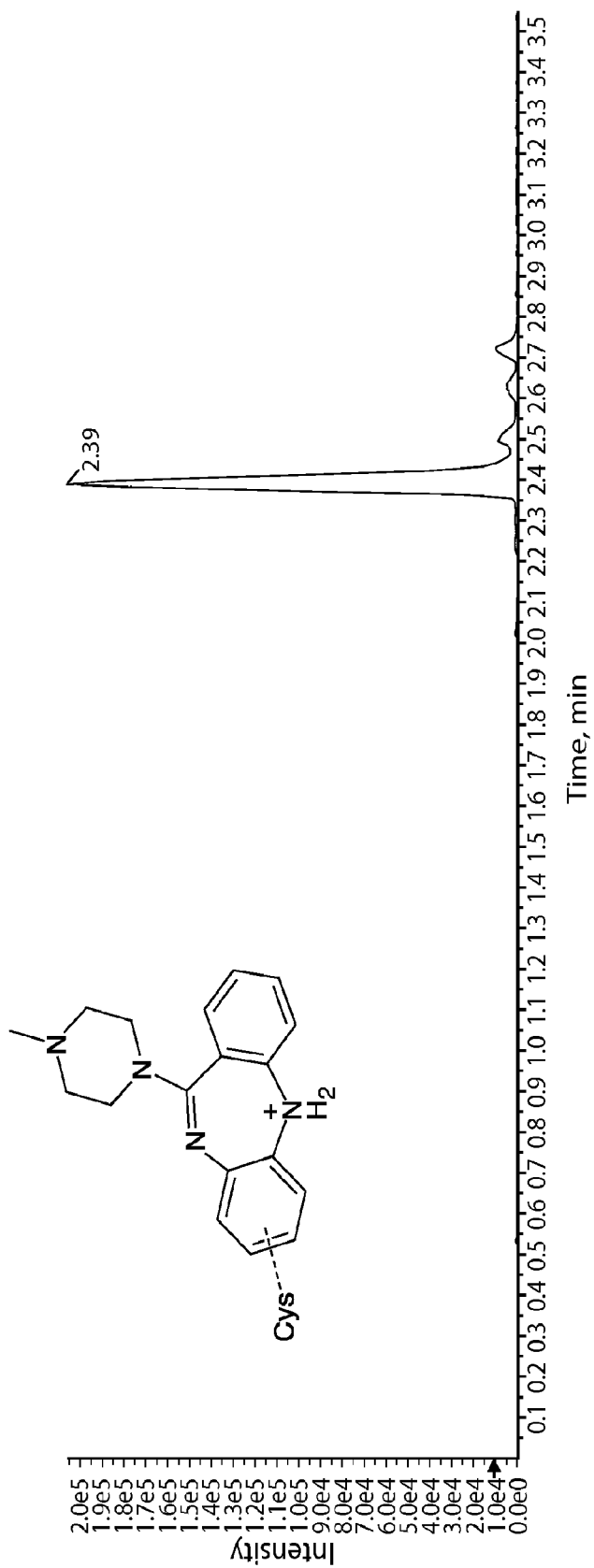
FIGS. 2A and 2B depict the LC-MS/MS analysis of cysteine adduct formation with clozapine (+TOF MS/MS (100-1000): 446.14+/−0.05 Da) plus two reactive clozapine metabolites.
Figure 2B:
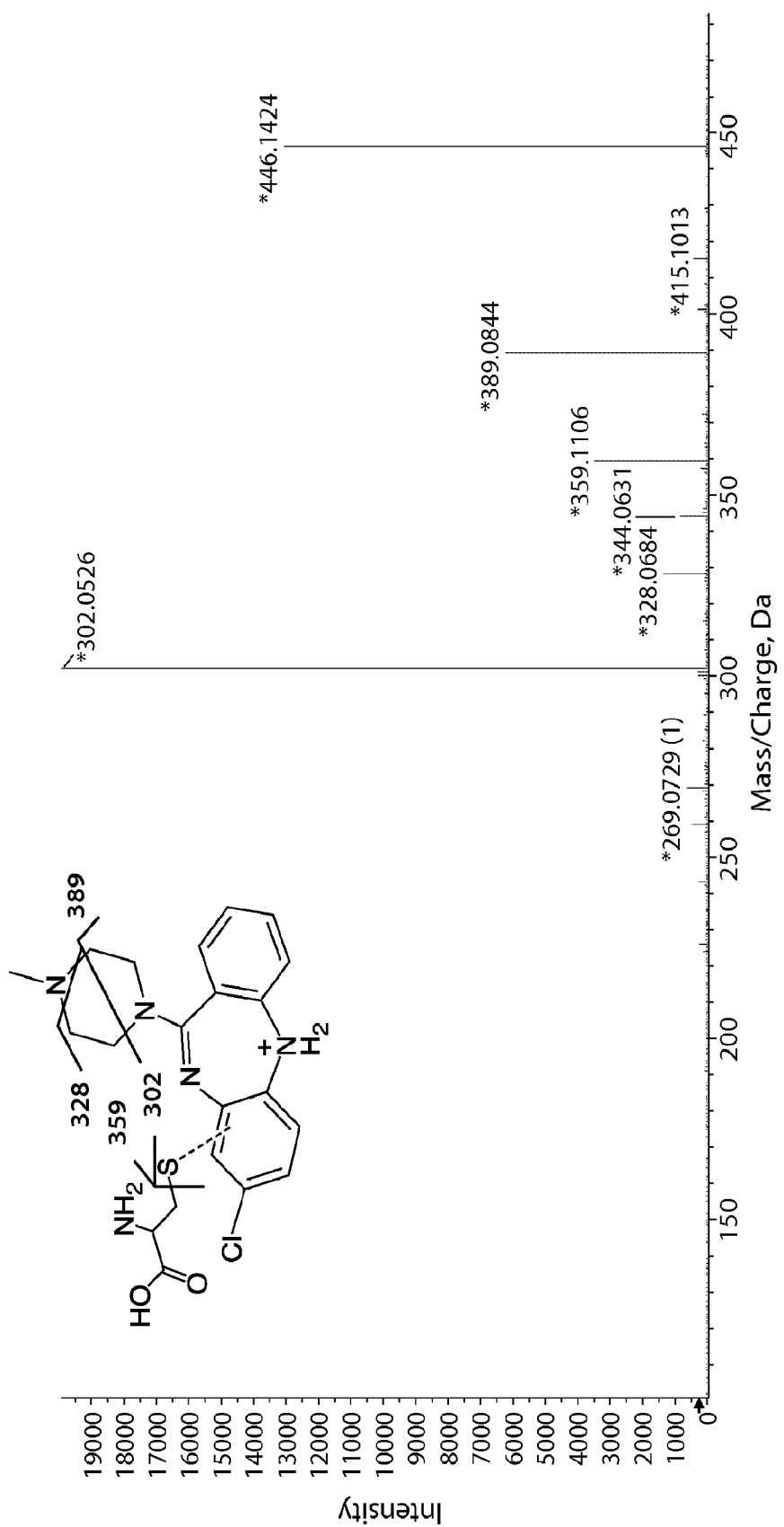
Figure 3A:
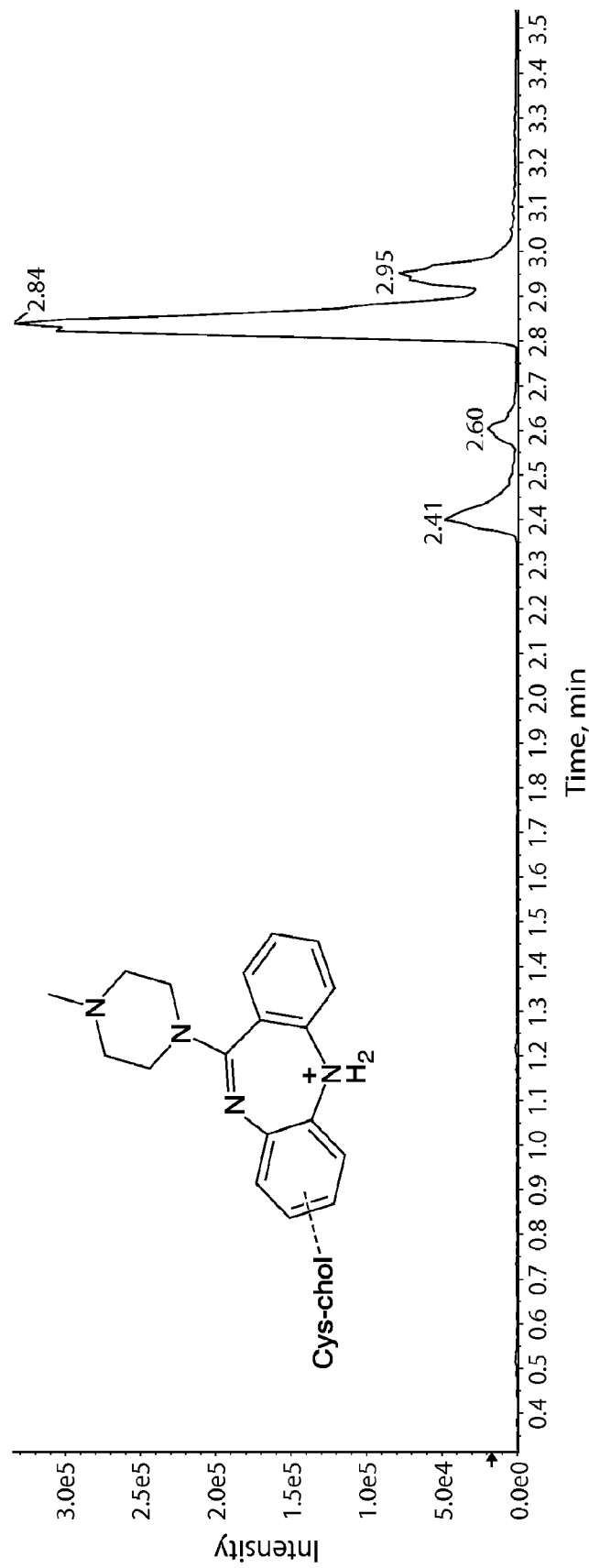
FIGS. 3A and 3B depict the LC-MS/MS analysis of cys-chol adduct formation with clozapine (+TOF MS-MS (100-1000): 530.25+/−0.05 Da) plus three reactive clozapine metabolites. Trapping reactive metabolites with cys-chol rather than GSH or cysteine demonstrates higher ionization efficiency and detection sensitivity.
Figure 3B:
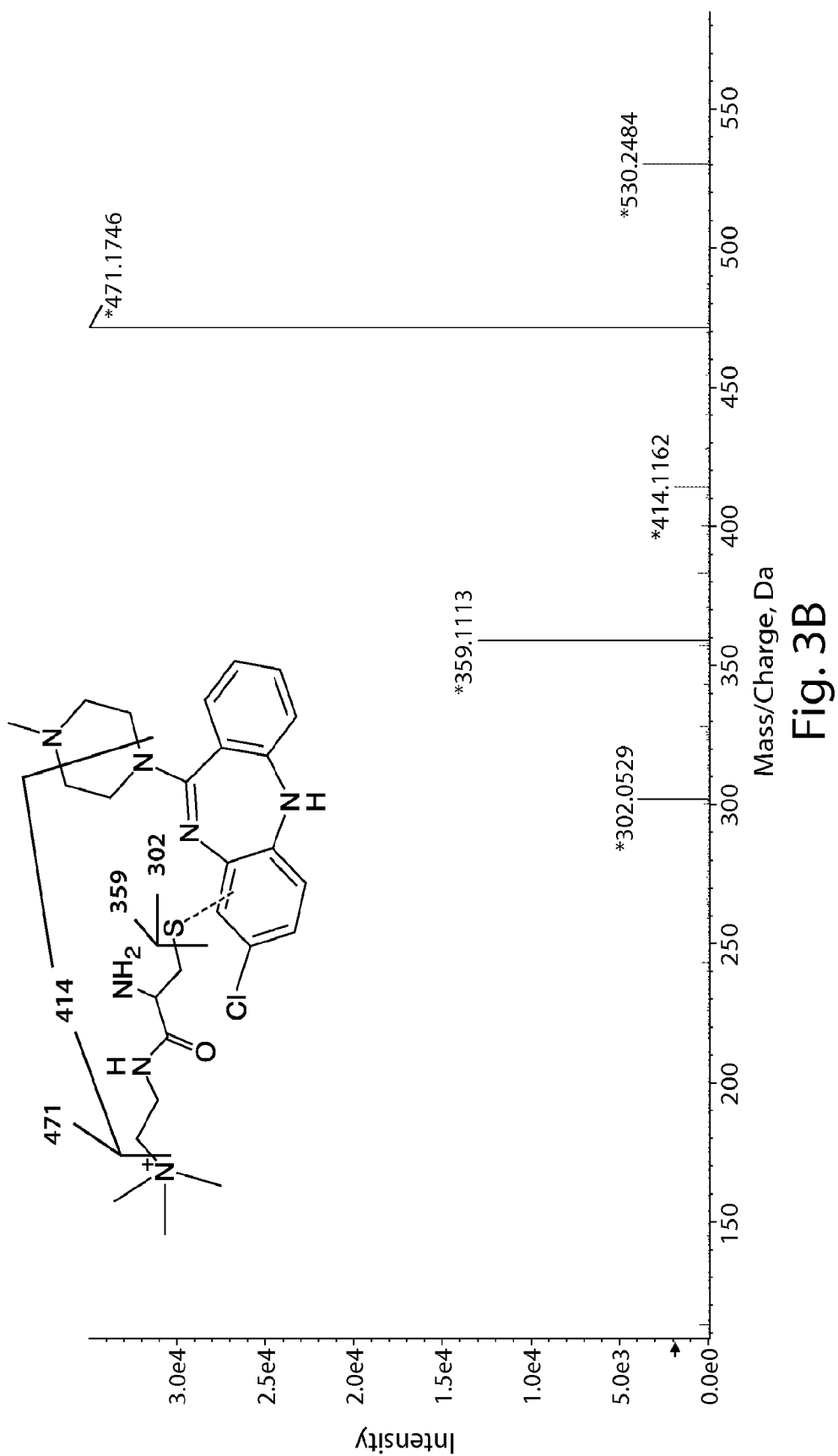
Figure 4:
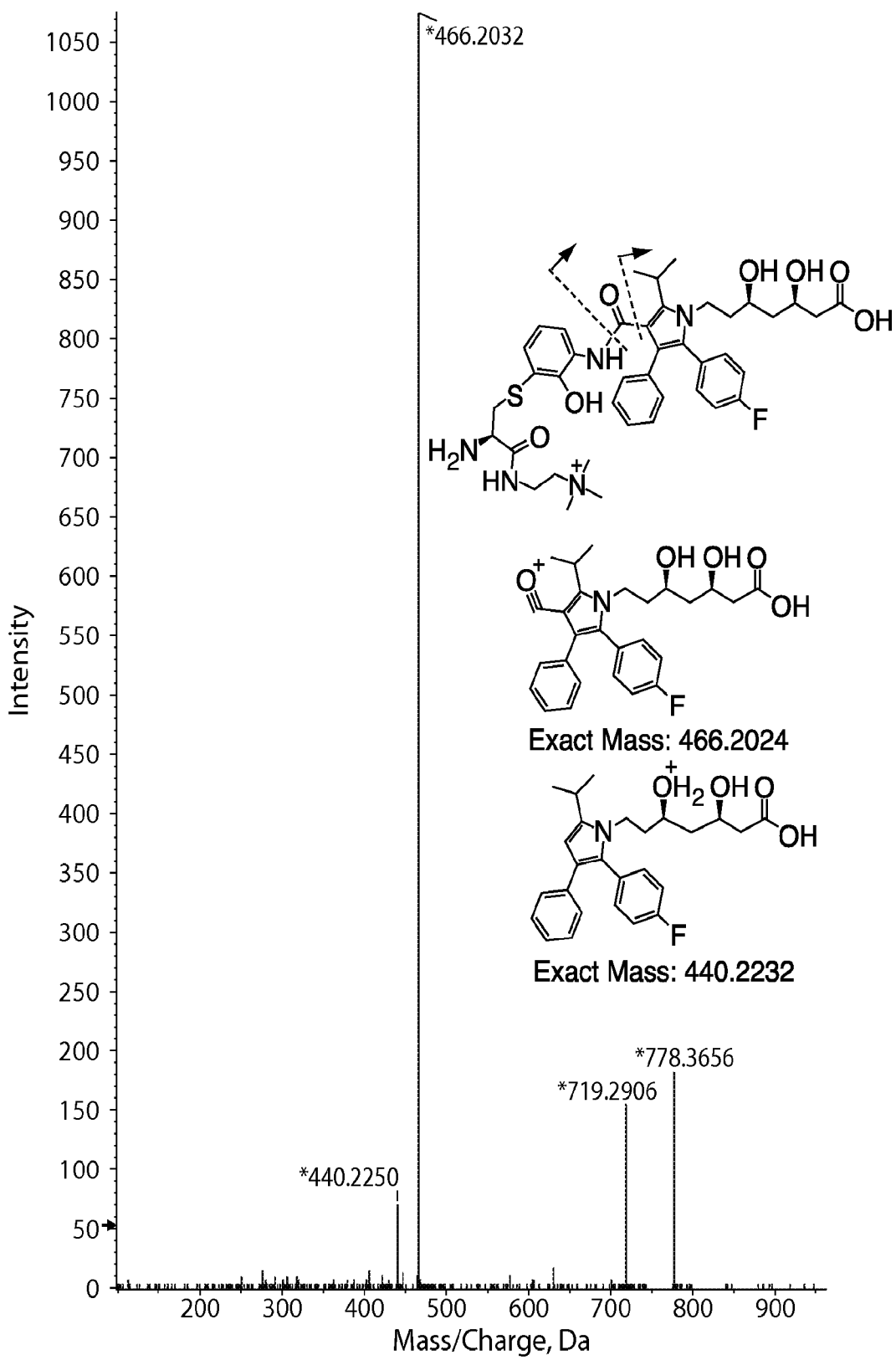
FIG. 4 depicts the LC-MS/MS analysis of an identified reactive cys-chol metabolite of Atrovastatin (Ator).
Figure 5:
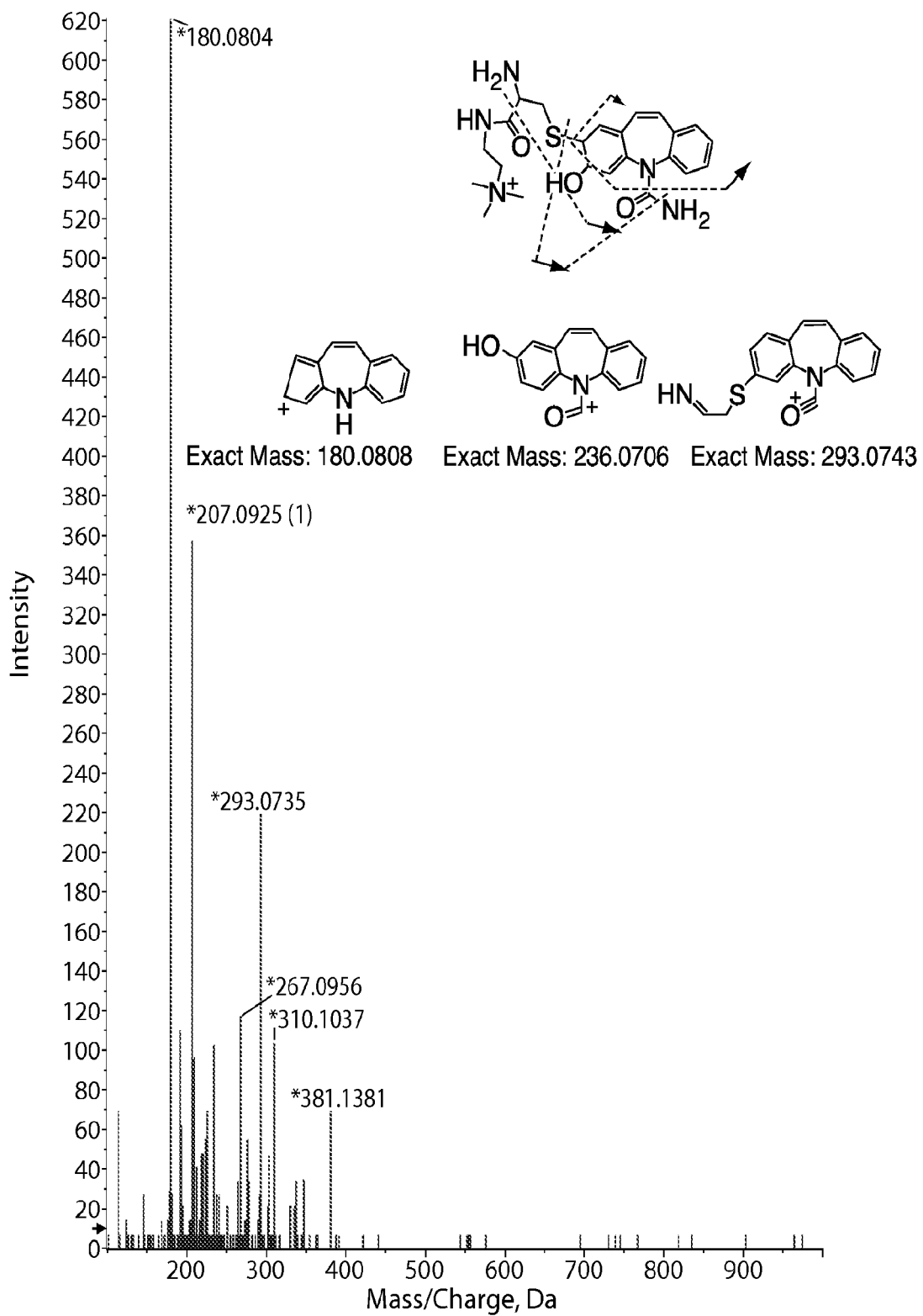
FIG. 5 depicts the LC-MS/MS analysis of an identified reactive cys-chol metabolite of Carbamazepine (CMZ).
Figure 6A:
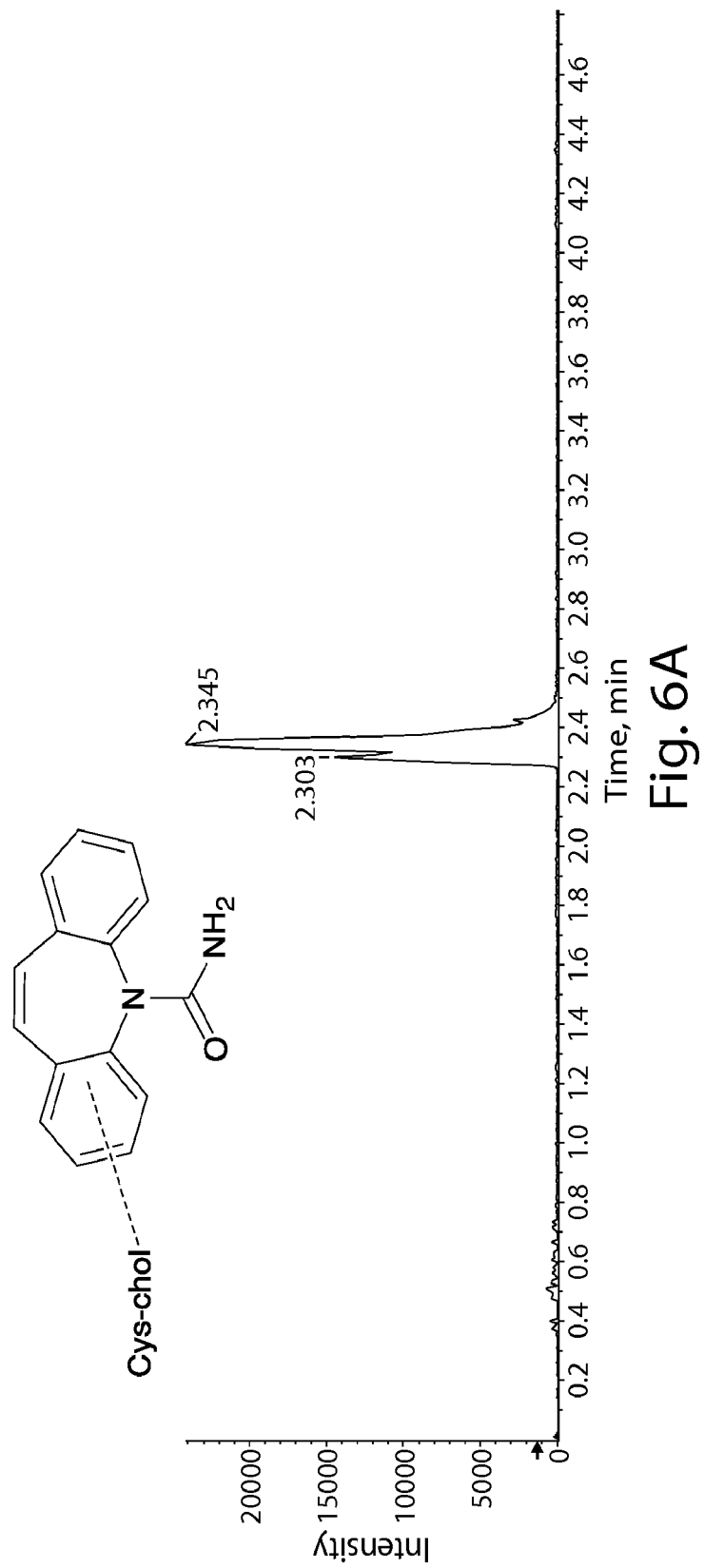
FIGS. 6A and 6B depict the LC-MS/MS analysis of cys-chol adduct formation with carbamazepine (+TOF MS/MS (100-1000): 440.21+/−0.05 Da). The same experiments with GSH and cysteine (Cys) as trapping agents did not produce any detectable conjugate.
Figure 6B:
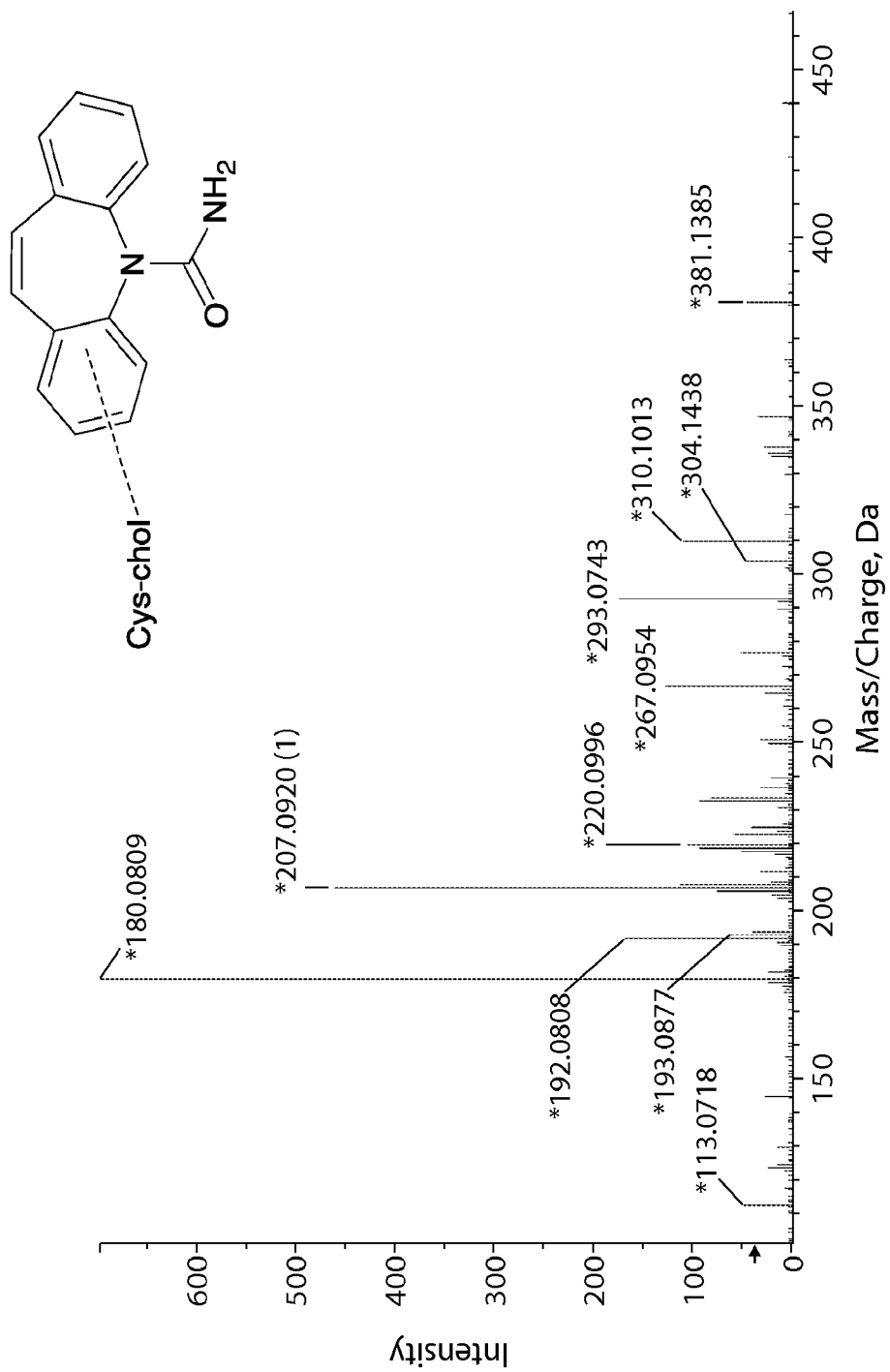
Figure 7A:
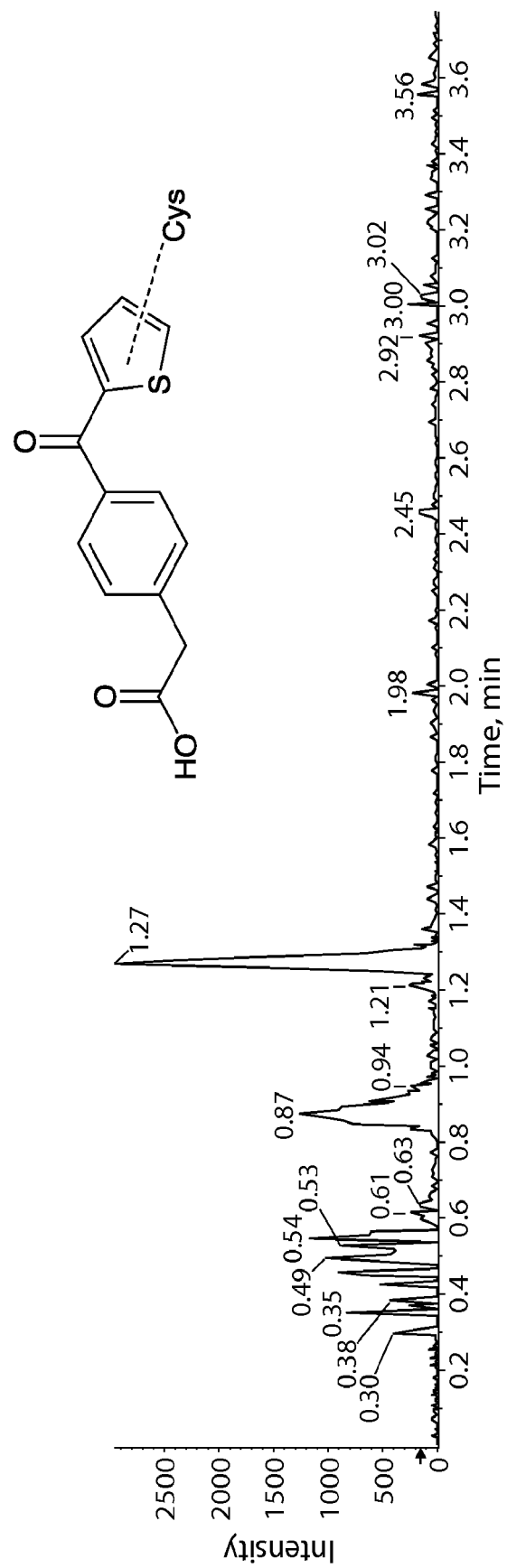
FIGS. 7A and 7B depict the LC-MS/MS analysis of cysteine (Cys) adduct formation with suprofen (+TOF MS/MS (100-1000): 380.06+/−0.05 Da).
Figure 7B:
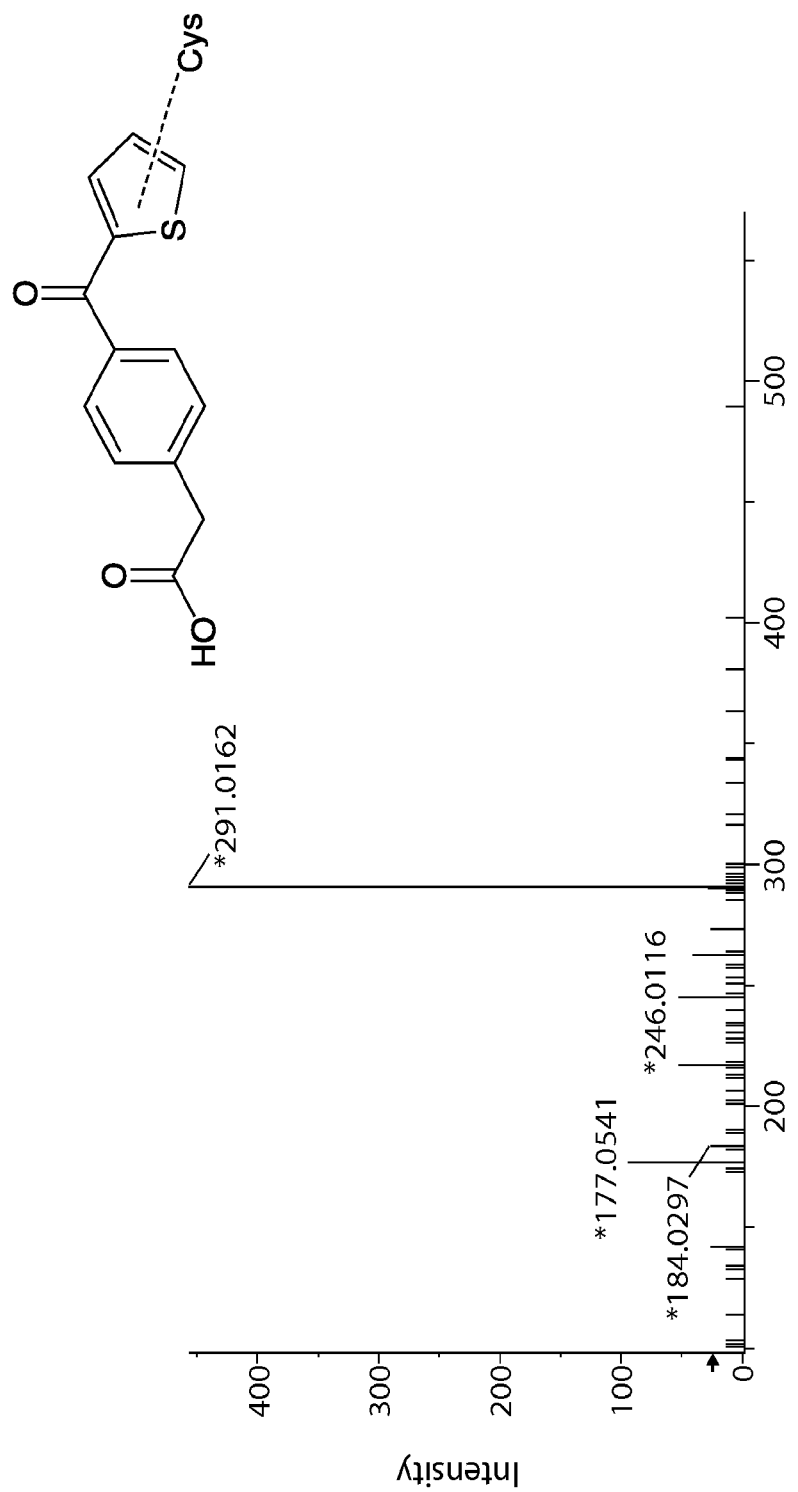
Figure 8A:
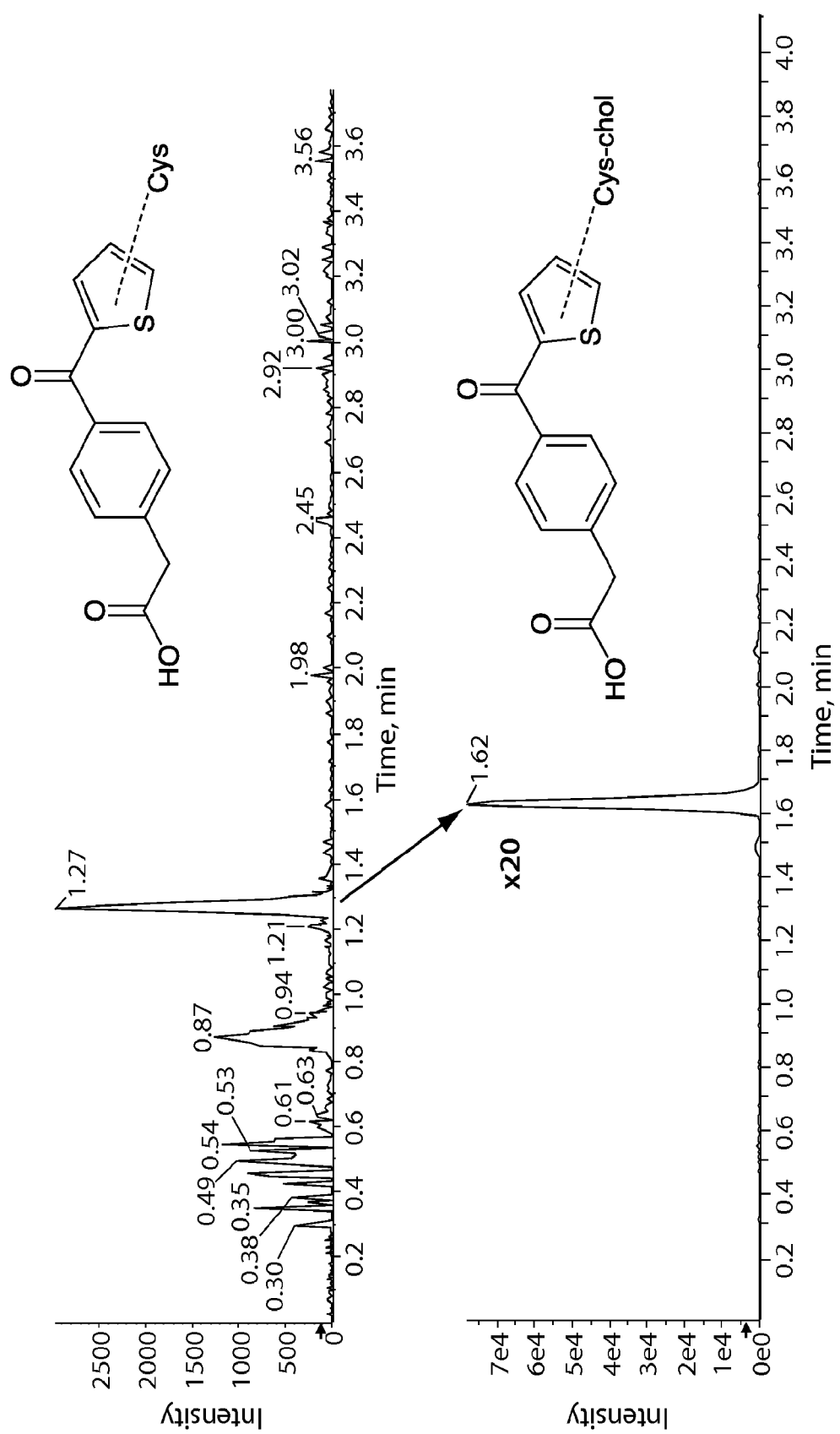
FIGS. 8A and 8B depict the LC-MS/MS analysis of cys-chol adduct formation with suprofen (+TOF MS/MS (100-1000): 464.17+/−0.05 Da), demonstrating higher ionization efficiency and detection sensitivity (20×) compared to Cys-adduct formation (see also FIG. 7A).
Figure 8B:
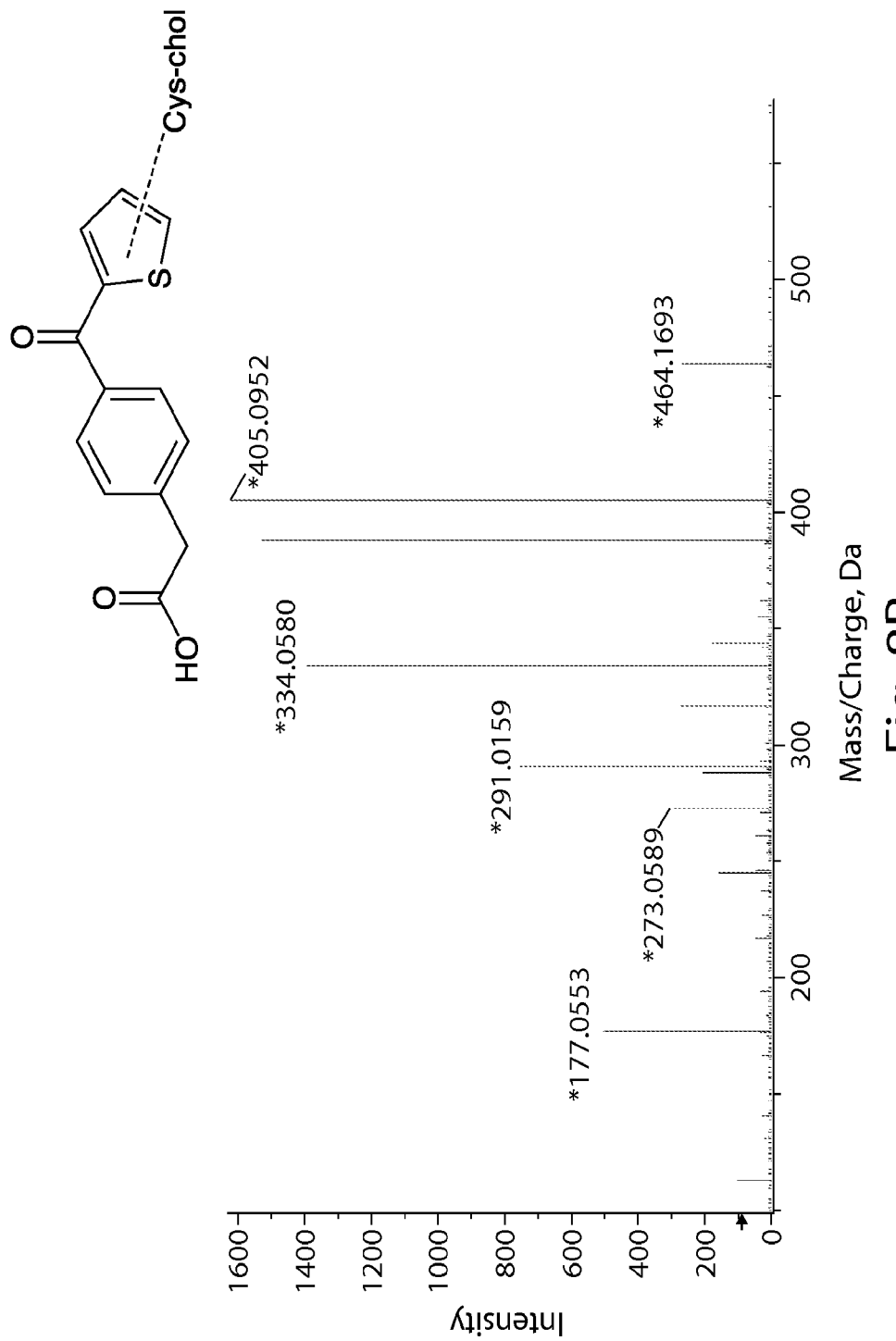

Table 3 provides a comparison of the sensitivity of the trapping clozapine and clozapine metabolites with GSH, cysteine (Cys), and the Cys-chol conjugate. See also FIGS. 1A, 1B, 2A, 2B, 3A, and 3B.

TABLE 3

| Clozapine-adduct | GSH m/z | GSH Detected (Y/N) | Cys m/z | Cys Detected (Y/N) | Cys-Chol m/z | Cys-Chol Detected (Y/N) | Cys-Chol signal relative to GSH signal | Cys-Chol signal relative to Cys signal |
|---|---|---|---|---|---|---|---|---|
| 1 Loss of Cl—2H + TR | 598 | ND | 412 | Yes | 496 | Yes |  | 5.6 |
| 2 Demethylation —2H + TR | 618 | ND | 432 | Yes | 516 | Yes |  | 1.9 |
| 3 —2H + TR | 632 | ND | 446 | Yes | 530 | Yes |  | 7.3 |
| 4 —2H + TR |  | Yes |  | Yes |  | Yes | 10.8 | 11.2 |
| 5 —2H + TR |  | Yes |  | Yes |  | Yes | 4.1 | 2.4 |
| 6 —2H + TR |  | ND |  | ND |  | Yes |  |  |
| 7 +O—2H + TR | 648 | ND | 462 | ND | 546 | Yes |  |  |
| 8 +O—2H + TR |  | ND |  | ND |  | Yes |  |  |
| 9 +O—2H + TR |  | Yes |  | Yes |  | Yes | 4.3 | 1.9 |
| 10 +O—2H + TR |  | Yes |  | ND |  | Yes | 6.3 |  |
| 11 +O + TR | 650 | ND | 464 | Yes | 548 | Yes |  | 3.6 |
| 12 +O + TR |  | Yes |  | Yes |  | Yes | 5.7 | 1.5 |

*ND = Not determined

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method for detecting a metabolite in a sample, the method comprising:
   contacting a sample comprising a metabolite and a compound of Formula (I) or (II):

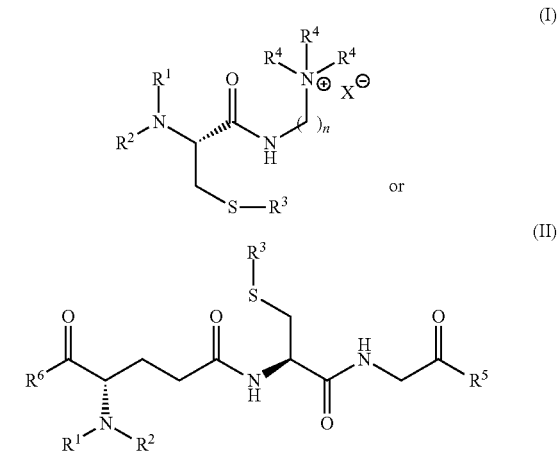

wherein the metabolite and the compound of Formula (I) or (II) react to form an adduct; and detecting the adduct;
   wherein:
   each instance of $R^1$ and $R^2$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=O)$R^A$, —C(=O)O$R^A$, —C(=O)N($R^A$)$_2$, or an amino protecting group, or $R^1$ and $R^2$ are joined to form a substituted or unsubstituted heterocyclic ring;
   each instance of $R^A$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a nitrogen protecting group when attached to a nitrogen atom, or two $R^A$ groups are joined to form a substituted or unsubstituted heterocyclic ring;
   $R^3$ is hydrogen;
   $R^5$ and $R^6$ are independently selected from —O$R^B$, —N($R^B$)$_2$, and a group of Formula (i):

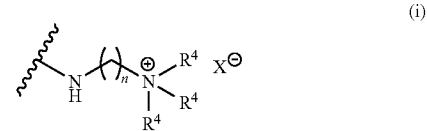

provided at least one of $R^5$ and $R^6$ is a group of Formula (i);
   each instance of $R^B$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a nitrogen protecting group when attached to a nitrogen atom, or two $R^B$ groups are joined to form a substituted or unsubstituted heterocyclic ring;

each instance of $R^4$ is independently substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, or two $R^4$ groups are joined to form a substituted or unsubstituted heterocyclic ring;

n is 1, 2, 3, 4, 5, or 6; and $X^-$ is a counter anion.

2. A method for detecting a metabolite in a sample, the method comprising:
contacting a test compound, an enzyme system, and a compound of Formula (I) or (II):

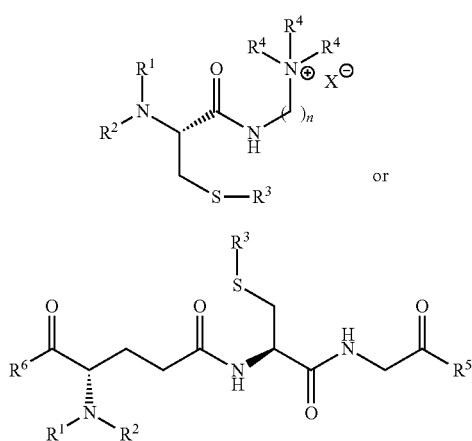

wherein the test compound is metabolized by the enzyme system to provide a metabolite; and the metabolite reacts with a compound of Formula (I) or (II) to form an adduct; and detecting the adduct;

wherein:
each instance of $R^1$ and $R^2$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=O) $R^4$, —C(=O)O$R^4$, —C(=O)N($R^4$)$_2$, or an amino protecting group, or $R^1$ and $R^2$ are joined to form a substituted or unsubstituted heterocyclic ring;

each instance of $R^4$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a nitrogen protecting group when attached to a nitrogen atom, or two $R^4$ groups are joined to form a substituted or unsubstituted heterocyclic ring;

$R^3$ is hydrogen;

$R^5$ and $R^6$ are independently selected from —O$R^B$, —N($R^B$)$_2$, and a group of formula (i):

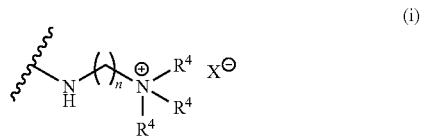

provided at least one of $R^5$ and $R^6$ is a group of formula (i);
each instance of $R^B$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a nitrogen protecting group when attached to a nitrogen atom, or two $R^B$ groups are joined to form a substituted or unsubstituted heterocyclic ring;

each instance of $R^4$ is independently substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, or two $R^4$ groups are joined to form a substituted or unsubstituted heterocyclic ring;

n is 1, 2, 3, 4, 5, or 6; and $X^-$ is a counter anion.

3. The method of claim 1, wherein the sample further comprises an enzyme system, and wherein the enzyme system is a P450 microsomal enzyme system.

4. The method of claim 1, wherein the adduct formation is initiated by addition of an NADPH-generating system or NADPH.

5. The method of claim 1, wherein the adduct is detected by mass spectrometry.

6. The method of claim 1, wherein the sample comprises a metabolite and a compound of Formula (I):

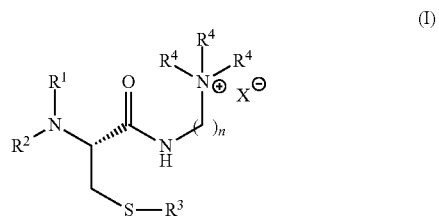

wherein:
each instance of $R^1$ and $R^2$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=O)$R^4$, —C(=O)O$R^4$, —C(=O) N($R^4$)$_2$, or an amino protecting group, or $R^1$ and $R^2$ are joined to form a substituted or unsubstituted heterocyclic ring;

each instance of $R^4$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a nitrogen protecting group when attached to a nitrogen atom, or two $R^A$ groups are joined to form a substituted or unsubstituted heterocyclic ring;

$R^3$ is hydrogen;

each instance of $R^4$ is independently substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, or two $R^4$ groups are joined to form a substituted or unsubstituted heterocyclic ring;

n is 1, 2, 3, 4, 5, or 6; and $X^-$ is a counteranion.

7. The method of claim 1, wherein the sample comprises a metabolite and a compound of Formula (II):

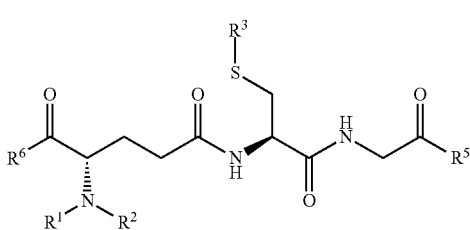

(II)

wherein:
each instance of $R^1$ and $R^2$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=O)$R^A$, —C(=O)O$R^A$, —C(=O)N($R^A$)$_2$, or an amino protecting group, or $R^1$ and $R^2$ are joined to form a substituted or unsubstituted heterocyclic ring;

each instance of $R^A$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a nitrogen protecting group when attached to a nitrogen atom, or two $R^A$ groups are joined to form a substituted or unsubstituted heterocyclic ring;

$R^3$ is hydrogen;

$R^5$ and $R^6$ are independently selected from —O$R^B$, —N($R^B$)$_2$, and a group of formula (i):

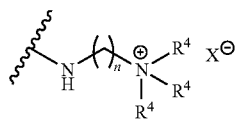

(i)

provided at least one of $R^5$ and $R^6$ is a group of formula (i);

each instance of $R^B$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a nitrogen protecting group when attached to a nitrogen atom, or two $R^B$ groups are joined to form a substituted or unsubstituted heterocyclic ring;

each instance of $R^4$ is independently substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, or two $R^4$ groups are joined to form a substituted or unsubstituted heterocyclic ring;

n is 1, 2, 3, 4, 5, or 6; and $X^-$ is a counteranion.

8. The method of claim 6, wherein $R^1$ is hydrogen, and $R^2$ is hydrogen, —C(=O)$R^A$, —C(=O)O$R^A$, —C(=O)N($R^A$)$_2$, or an amino protecting group.

9. The method of claim 8, wherein $R^1$ is hydrogen and $R^2$ is —C(=O)$R^A$, —C(=O)O$R^A$, or —C(=O)NH$R^A$, wherein $R^A$ is a group of formula:

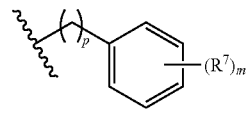

wherein p is 0, 1, or 2; m is 1, 2, 3, 4, or 5; and $R^7$ is halogen.

10. The method of claim 9, wherein $R^7$ is bromo or fluoro.

11. The method of claim 7, wherein $R^B$ is a group of formula:

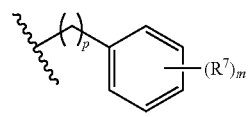

wherein p is 0, 1, or 2; m is 1, 2, 3, 4, or 5; and $R^7$ is halogen.

12. The method of claim 11, wherein $R^7$ is bromo or fluoro.

13. The method of claim 6, wherein $R^3$ is hydrogen.

14. The method of claim 6, wherein each instance of $R^4$ is independently substituted or unsubstituted alkyl.

15. The method of claim 6, wherein n is 2.

16. The method of claim 6, wherein $X^-$ is a chloride counteranion.

17. The method of claim 6, wherein the compound of Formula (I) is of Formula (I-c):

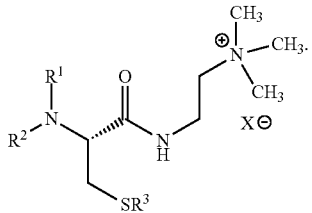
(I-c)
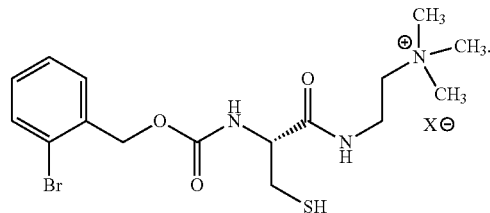
18. The method of claim 6, wherein the compound of Formula (I) is selected from the group consisting of:
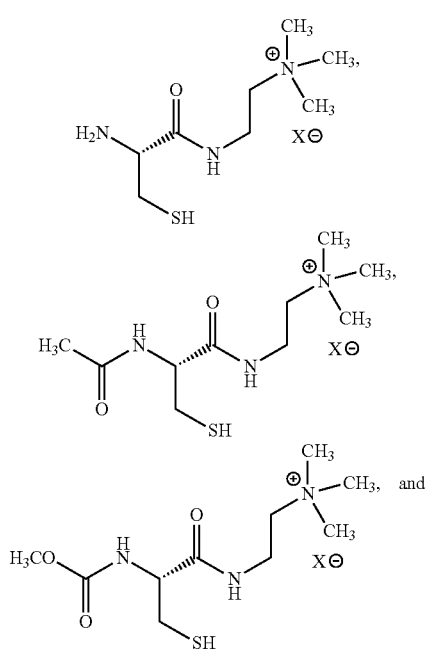
19. The method of claim 7, wherein the compound of Formula (II) is of Formula (II-d) or (II-g):
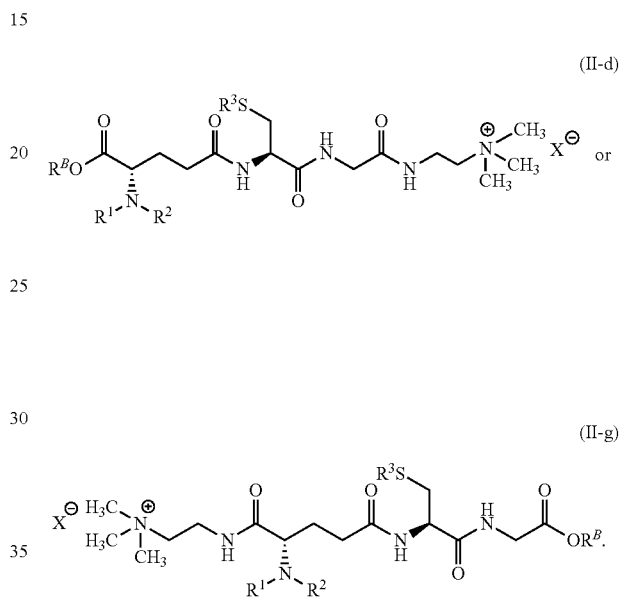
20. The method of claim 7, wherein the compound of Formula (II) is selected from the group consisting of:
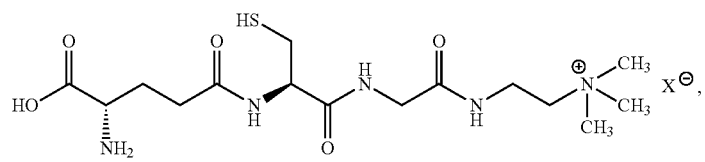
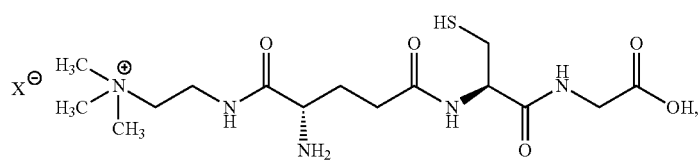
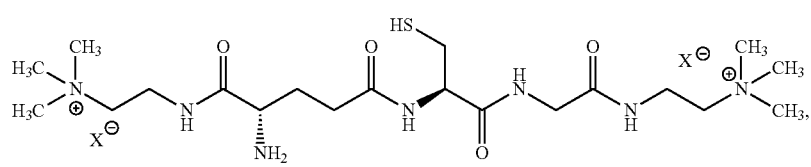

-continued
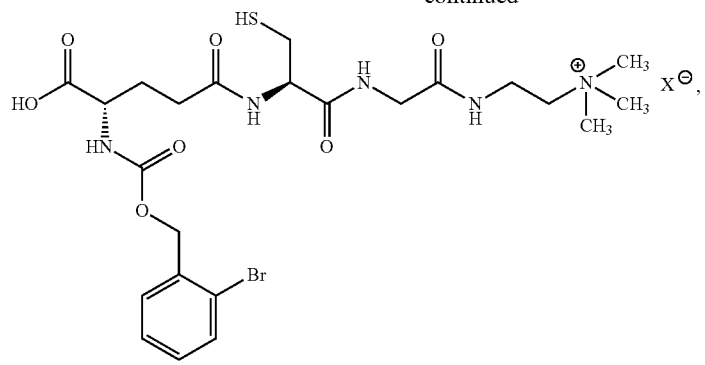
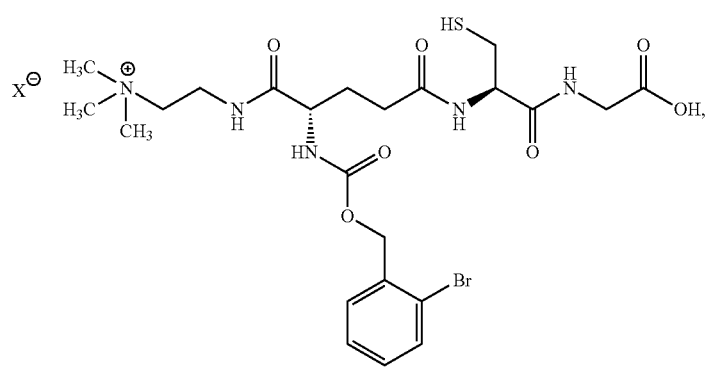
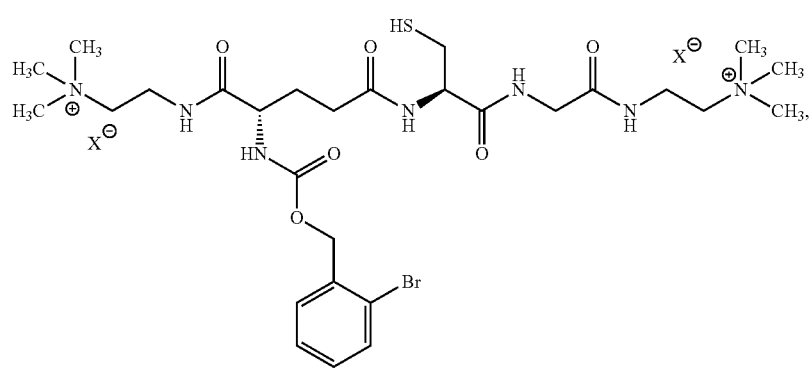
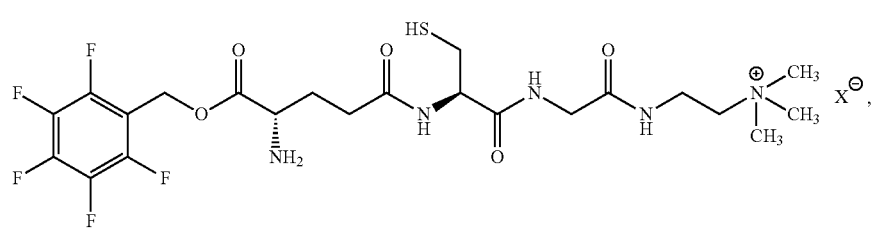
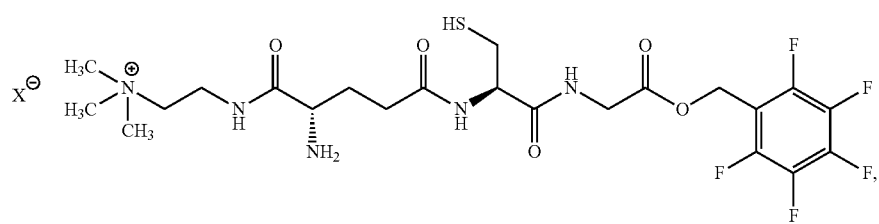

-continued
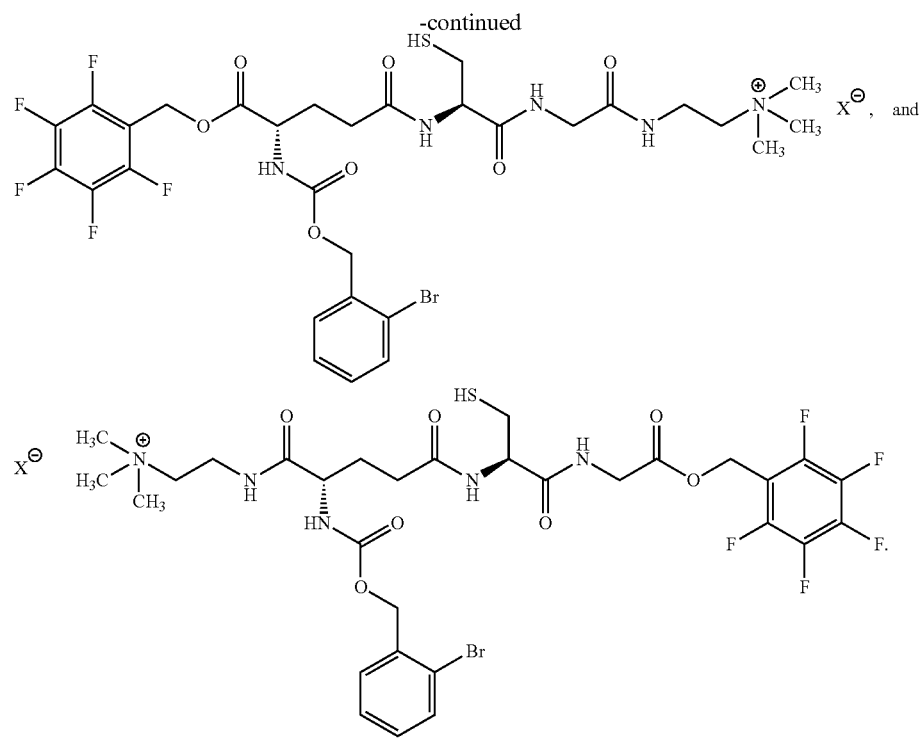
* * * * *